(12) United States Patent
Nagamatsu

(10) Patent No.: US 12,351,583 B2
(45) Date of Patent: Jul. 8, 2025

(54) TRIAZOLOPYRIMIDINES BASED ON THYMINE NUCLEOBASE AND METHODS FOR PRODUCING THEM

(71) Applicant: TERA STONE CO., LTD, Yokohama (JP)

(72) Inventor: Tomohisa Nagamatsu, Kumamoto (JP)

(73) Assignee: CHEMITERAS, INC., Yokohama (JP)

( * ) Notice: Subject to any disclaimer, the term of this patent is extended or adjusted under 35 U.S.C. 154(b) by 895 days.

(21) Appl. No.: 17/600,408

(22) PCT Filed: Mar. 31, 2020

(86) PCT No.: PCT/JP2020/014810
§ 371 (c)(1),
(2) Date: Sep. 30, 2021

(87) PCT Pub. No.: WO2020/204024
PCT Pub. Date: Oct. 8, 2020

(65) Prior Publication Data
US 2022/0194950 A1 Jun. 23, 2022

(30) Foreign Application Priority Data
Apr. 3, 2019 (JP) ................................. 2019-071525

(51) Int. Cl.
C07D 487/04 (2006.01)
A61P 35/00 (2006.01)

(52) U.S. Cl.
CPC ............ *C07D 487/04* (2013.01); *A61P 35/00* (2018.01)

(58) Field of Classification Search
CPC .................................................. C07D 487/04
See application file for complete search history.

(56) References Cited

U.S. PATENT DOCUMENTS

| | | | |
|---|---|---|---|
| 4,405,780 A | 9/1983 | Wagner | |
| 4,528,288 A | 7/1985 | Wade | |

(Continued)

FOREIGN PATENT DOCUMENTS

| | | |
|---|---|---|
| JP | 2002-037787 | 2/2002 |
| WO | 88/02370 | 7/1991 |

OTHER PUBLICATIONS

CA Reg No. 1935655-44-9, entered into STN on Jun. 20, 2016. (Year: 2016).*

(Continued)

*Primary Examiner* — Adam C Milligan
*Assistant Examiner* — Karen Cheng

(74) *Attorney, Agent, or Firm* — JMB Davis Ben-David

(57) ABSTRACT

The present invention provides novel triazolopyrimidines derived from nucleobase thymine, and methods of producing the same, as well as various biologically active substances obtained by the methods, particularly antitumor agents. The triazolopyrimidine compounds represented by the following formulas (I) to (VIII) (wherein R represents a hydrogen atom, an alkyl group, or an aryl group) and methods of producing the same.

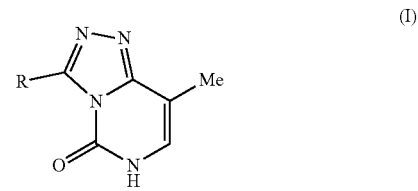

(I)

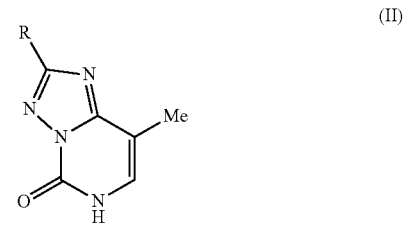

(II)

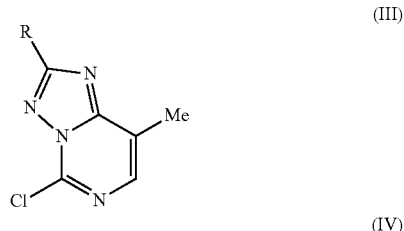

(III)

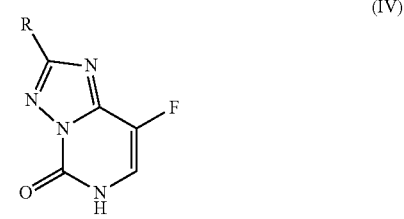

(IV)

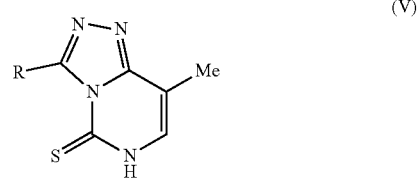

(V)

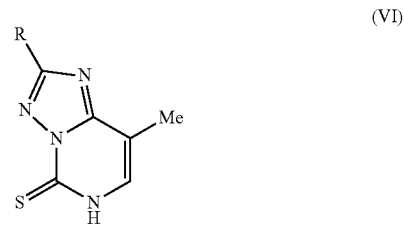

(VI)

(Continued)

-continued

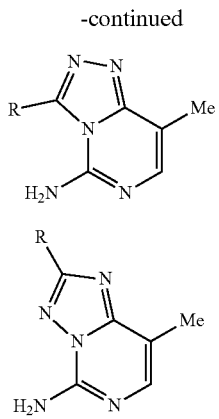

10 Claims, No Drawings

(56) References Cited

U.S. PATENT DOCUMENTS

| | | | |
|---|---|---|---|
| 4,572,910 | A | 2/1986 | Wade |
| 4,831,013 | A | 5/1989 | Francis |
| 2003/0143199 | A1 | 7/2003 | Carson et al. |
| 2006/0052023 | A1 | 3/2006 | Lauridsen et al. |
| 2007/0208010 | A1* | 9/2007 | Weber .................. C07D 487/04 544/251 |
| 2009/0105277 | A1 | 4/2009 | Kadowaki et al. |
| 2016/0176882 | A1 | 6/2016 | Chan et al. |

OTHER PUBLICATIONS

Notification concerning transmittal of international preliminary report on patentability (Form PCT/IB/326) for Corresponding International Patent Application PCT/JP2020/014810.

International preliminary report on patentability (Form PCT/IB/373) for Corresponding International Patent Application PCT/JP2020/014810.

Notification of transmittal of translation of the international preliminary report on patentability (Form PCT/IB/338) for Corresponding International Patent Application PCT/JP2020/014810.

Translation of International preliminary report on patentability (Form PCT/IB/373) for Corresponding International Patent Application PCT/JP2020/014810.

STN Registry, RN 1934600-89-1, Jun. 19, 2016.

STN Registry, RN 1367943-51-8, Apr. 15, 2012.

File POC13 246 trichloropyridine.png; Available online at commons.wikimedia.org/wiki.file:POC_13246trichloropyridine.png, drawings, summary, edited Nov. 9, 2015, retrieved Jun. 12, 2020.

Nagamatsu et al "The First Reliable, General Synthesis of the 5-Oxo Derivatives of 5,6-Dihydro-1,2,4-triazolo[4,3-c]pyrimidine and the Rates of Isomerization of the [4,3-c] Compounds into Their [1,5-c] Isomers" Heterocycles, 57:631-636, 2002.

Nagamatsu et al "Research Article Previous Next Contents vol. 31 (11) Isomerizations akin to the Dimroth rearrangement. IV. Formation of simple s-Triazolo[1,5-c]pyrimidines via their [4,3-c] isomers", Australian Journal of Chemistry 31(11) 2505-2515 Published: 1978, found online at https://doi.org/10.1071/CH9782505.

Nagamatsu et al "Purine analogues as amplifiers of phleomycin. II. Some s-Triazolo[4,3-a]pyridines, s-Triazolo[4,3- or 1,5-a]pyrimidines and s-Triazolo[3,4-b]benzothiazoles", Australian Journal of Chemistry 31(2) 397-404 Published: 1978, seen online at https://doi.org/10.1071/CH9780397.

Nagamatsu et al "Purine Analogues as Amplifiers of Phleomycin. V. Thioethers of Several Heterocyclic Systems with One or Two Rings", Australian Journal of Chemistry 32(12) 2713-2726 Published: 1979 seen online at https://doi.org/10.1071/CH9792713.

Chinese Office action (including English machine translation of Office Action) Patent Application No. CN 202080022274.4 Date of Drafting: Mar. 23, 2024.

Extended European Search Report of corresponding EP patent application, Patent Application No. 20785204.7, Date of Drafting: Dec. 6, 2022.

Registry 1934600-89-1, XP 55980876, Patent Cited Document disclosed in Extended European Search Report of corresponding EP patent application.

Database Registry XP 55747637, Patent Cited Document disclosed in Extended European Search Report of corresponding EP patent application.

Office Action from JPO (English machine translation of Office Action), Patent Application No. JP2021-512147, Date of Drafting: Jan. 24, 2023.

Office action issued by CNIPA in corresponding Patent Application No. 202080022274.4, Date of Drafting: Aug. 25, 2023.

Brown et al, Australian Journal of Chemistry, vol. 33, No. 5, pp. 1147-1152, 1980.

Canadian Patent Office, Examination Report for Canadian Patent Application No. 3,135,449 Date of Issuance: Jan. 27, 2025, pp. 1-5, Canada.

Korean Office Action, parallel application, Patent Application No. KR10-2021-7029903.

\* cited by examiner

TRIAZOLOPYRIMIDINES BASED ON THYMINE NUCLEOBASE AND METHODS FOR PRODUCING THEM

TECHNICAL FIELD

The present invention relates to novel compounds of triazolopyrimidines derived from the nucleobases such as thymine and uracil, and methods for producing the same, as well as various biologically active substances obtained by the methods, particularly antitumor agents.

BACKGROUND ART

Fluorouracil (5-fluorouracil, 5-FU) has been evaluated as an antineoplastic agent by Heidelberger et al. in extensive basic and clinical studies, is a fluoropyrimidine-based antimetabolite and antineoplastic agents (anticancer agent). Its structure is that in which the hydrogen atom at the 5-position in uracil is replaced to a fluorine atom. Since the 1990s, improvements, such as prodrugization, of fluorouracil have been made, and their drugs (internal drugs) expected to have stronger effects have been developed and marketed. These drugs are used for relief of subjective and objective symptoms of the following diseases: gastric cancer, liver cancer, colon/rectal cancer, breast cancer, pancreatic cancer, cervical cancer, endometrial cancer, ovarian cancer, and the like. Furthermore, these drugs are used in combination with other anticancer agents or radiotherapy for the following diseases: esophageal cancer, lung cancer, head and neck tumor, and the like. Although the above existing drugs and their metabolites inhibit nucleic acid synthesis (antimetabolite) and exhibit antitumor effects, treatment using these drugs is carried out based on the judgment of a doctor who is familiar with the treatment because strong side effects are expected. The following serious side effects are known such as dehydration, severe enteritis, bone marrow depression, shock, anaphylactic symptoms, leukoencephalopathy, congestive heart failure, myocardial infarction, resting angina, acute renal failure, interstitial pneumonia, liver dysfunction, jaundice, gastrointestinal ulcer, severe stomatitis, acute pancreatitis, hyperammonemia with consciousness disorder, liver/biliary tract disorder (cholecystitis, bile duct necrosis, liver parenchymal disorder, etc.) and limb syndrome, olfactory disorder, and the like.

Meanwhile, among various triazolopyrimidines, compounds having [1,2,4]triazolo[4,3-c]pyrimidine skeleton are known to produce more stable compounds having [1,2,4]triazolo[1,5-c]pyrimidine skeleton by undergoing Dimroth rearrangement readily under acid or alkaline presence or thermal conditions (see Non-Patent Document 1 below, which is incorporated herein by reference in their entirety.). A variety of their derivatives have been synthesized, and their effects such as potentiating effects on phleomycin have been reported (see Non-patent Documents 2 and 3 below, which are incorporated herein by reference in their entirety.). In addition, regarding structural isomers of 8-methyl derivatives of triazolopyrimidines derived from nucleobase thymine, the following compounds only have been reported in a rapid publication: derivatives of 8-methyl-[1,2,4]triazolo[4,3-c]pyrimidin-5(6H)-ones with a substituent at the 3-position, and 8-methyl-[1,2,4]triazolo[1,5-c]pyrimidin-5(6H)-ones with a substituent at the 2-position, wherein the substituent is a hydrogen atom, a methyl group or a phenyl group (see Non-Patent Document 4 below, which is incorporated herein by reference in their entirety.).

CITATION LIST

Non-Patent Documents

Non-Patent Document 1:
D. J. Brown and T. Nagamatsu et al., *Aust. J. Chem.*, 31, pp. 2505-15 (1978)
Non-Patent Document 2:
D. J. Brown and T. Nagamatsu et al., *Aust. J. Chem.*, 31, pp. 397-404 (1978) and 32, pp. 2713-26 (1979)
Non-Patent Document 3:
D. J. Brown and T. Nagamatsu et al., *Aust. J. Chem.*, 32, pp. 2713-26 (1979)
Non-Patent Document 4:
T. Nagamatsu et al., *Heterocycles*, 57, No. 4, pp. 631-636 (2002)

SUMMARY OF THE INVENTION

Problems to be Solved by the Invention

Despite those various physiological activities such as antitumor activities are expected, structural isomers of 8-methyl derivatives of triazolopyrimidines derived from nucleobase thymine other than the aforementioned conventional compounds, 8-methyl-[1,2,4]triazolo[4,3-c]pyrimidin-5(6H)-ones (I) and 8-methyl-[1,2,4]triazolo[1,5-c]pyrimidin-5(6H)-ones (II) compounds have not yet been reported. Moreover, the following compounds also have not yet been reported: 5-chloro-8-methyl-[1,2,4]triazolo[1,5-c]pyrimidine compound (III); 8-fluoro-[1,2,4]triazolo[1,5-c]pyrimidin-5(6H)-one compound (IV) which can be derived from 5-fluorouracil known as an anticancer agent; 8-methyl-[1,2,4]triazolo[4,3-c]pyrimidin-5(6H)-thione compound (V); 8-methyl-[1,2,4]triazolo[1,5-c]pyrimidin-5(6H)-thione compound (VI), 8-methyl-[1,2,4]triazolo[4,3-c]pyrimidin-5-amine compound (VII); and 8-methyl-[1,2,4]triazolo[1,5-c]pyrimidine-5-amine compound (VIII).

Therefore, for the purpose of searching anti-malignant tumor drugs having fewer side effects and more effective activities on stem cancer cells than those of 5-FU analog compounds known as a potent anticancer agent, the present inventors have been focusing on bicyclic triazolopyrimidine skeleton derived from thymine or 5-FU, and conducting its synthetic research.

Accordingly, it is a major objective of the present invention to provide a variety of novel triazolopyrimidine derivatives having antitumor activity.

Means of Solving the Problems

As a result of extensive efforts to achieve the above objective, the present inventors found that triazolopyrimidine derivatives with a specific structure have antitumor activity and are useful as drugs, and thus they proceeded the present invention. The present specification describes the production of novel compounds having [1,2,4]triazolo[4,3-c]pyrimidin-5(6H)-one skeleton, their rearrangement isomer compounds having [1,2,4]triazolo[1,5-c]pyrimidin-5(6H)-one skeleton and their analog compounds, and describes their antitumor activity.

Therefore, according to the present invention, the following aspects [1] to [16] are provided.

[1] An 8-methyl-[1,2,4]triazolo[4,3-c]pyrimidin-5(6H)-one compound represented by the following general formula (I):

(General formula (I))

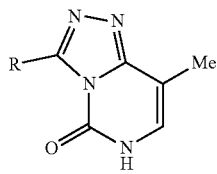

(I)

wherein R represents an alkyl group or an aryl group.

[2] An 8-methyl-[1,2,4]triazolo[1,5-c]pyrimidin-5(6H)-one compound represented by the following general formula (II)

(General formula (II))

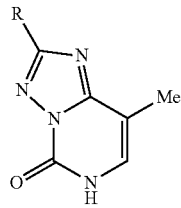

(II)

wherein R represents an alkyl group or an aryl group.

[3] A 5-chloro-8-methyl-[1,2,4]triazolo[1,5-c]pyrimidine compound represented by the following general formula (III):

(General formula (III))

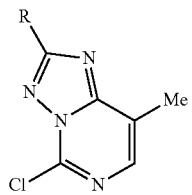

(III)

wherein R represents an aryl group.

[4] An 8-fluoro-[1,2,4]triazolo[1,5-c]pyrimidin-5(6H)-one compound represented by the following general formula (IV):

(General formula (IV))

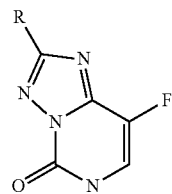

(IV)

wherein R represents a hydrogen atom, an alkyl group, or an aryl group.

[5] An 8-methyl-[1,2,4]triazolo[4,3-c]pyrimidin-5(6H)-thione compound represented by the following general formula (V):

(General formula (V))

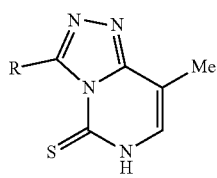

(V)

wherein R represents a hydrogen atom, a methyl group, or a phenyl group.

[6] An 8-methyl-[1,2,4]triazolo[1,5-c]pyrimidin-5(6H)-thione compound represented by the following general formula (VI):

(General formula (VI))

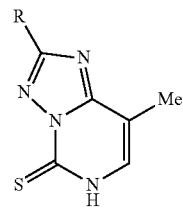

(VI)

wherein R represents a hydrogen atom, a methyl group, or a phenyl group.

[7] An 8-methyl-[1,2,4]triazolo[4,3-c]pyrimidin-5-amine compound represented by the following general formula (VII):

(General formula (VII))

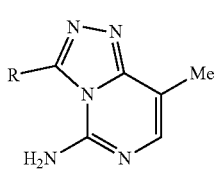

(VII)

wherein R represents a hydrogen atom, a methyl group, or a phenyl group.

[8] An 8-methyl-[1,2,4]triazolo[1,5-c]pyrimidin-5-amine compound represented by the following general formula (VIII):

(General formula (VIII))

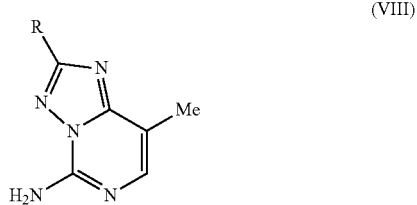

(VIII)

wherein R represents a hydrogen atom, a methyl group, or a phenyl group.

[9] A pharmaceutical composition, containing as an active ingredient at least one compound selected from the group consisting of the compounds according to [1] to [8].

[10] An antitumor composition, containing as an active ingredient at least one compound selected from the group consisting of the compounds according to [1] to [8].

[11] Use of at least one compound selected from the group consisting of the compounds according to [1] to [8] for producing a pharmaceutical composition.

[12] A method for treating tumors, including administering an effective amount of at least one compound selected from the group consisting of the compounds according to [1] to [8].

[13] A method of producing the compound according to any one of [1], [2], [4], [5] and [7], including the step of reacting an aldehyde hydrazone compound with an oxidizing agent to obtain a triazolopyrimidine compound.

[14] A method of producing the compound according to [2] or [8], including the step of heating a [1,2,4]triazolo[4,3-c]pyrimidine compound in a solvent to obtain a [1,2,4]triazolo[1,5-c]pyrimidine compound.

[15] A method of producing the compound according to [3], including the step of heating a triazolopyrimidine compound having an oxo group at the 5-position thereof under reflux in phosphorus oxychloride to obtain a triazolopyrimidine compound having a chloro group at the 5-position thereof.

[16] A method of producing the compound according to any one of [4] to [8], including the step of reacting a hydrazino compound with orthoester to obtain a triazolopyrimidine compound.

Effect of the Invention

The triazolopyrimidine compounds according to one aspect of the present invention have cancer cell proliferation inhibitory activity, and are a fluorinated pyrimidine-based antimetabolite agent, as well as they are condensation compounds containing a structure of 5-FU (5-fluorouracil, having structure in which the hydrogen atom at the 5-position of uracil is replaced by fluorine atom) or a thymine structure of nucleic acid base, which have already been used clinically as an antitumor agent. Therefore, a composition containing the triazolopyrimidine compound according to one aspect of the present invention is useful as an antitumor drug (anticancer agent) for treating various tumors.

DESCRIPTION OF EMBODIMENTS

While a triazolopyrimidine compound according to one aspect of the present invention, a production method thereof, and a composition containing the foregoing compound will now be described in further details, the scope of the present invention is not limited to what is described in this section; rather, the present invention may take various other forms to the extent that its objective is achieved.

As used herein, the term "tumor" is not particularly limited as long as it is used in the meaning commonly used by those skilled in the art. For example, it refers to a mass of tissue formed by autonomous overgrowth of cells out of control in the living bodies.

As used herein, the term "antitumor" refers to inhibition of proliferation of cells constituting a tumor, suppression of infiltration of cells constituting a tumor, or attenuation or death of cells constituting a tumor. The term "antitumor activity" thus refers to the above-mentioned activities such as inhibition of proliferation of cells.

The triazolopyrimidine compounds according to one aspect of the present invention are represented by general formulas (I) to (VIII), wherein R is as defined above. Examples of the alkyl group represented by R include a liner or branched lower alkyl group having a carbon number of 1 to 7, such as methyl, ethyl, propyl and butyl groups. Examples of the aryl group include a phenyl group and a phenyl group having a substituent. Examples of substituents modifying a phenyl group (hereinafter referred to as "substituent for phenyl group") may include a halogen atom, an alkyl group, an alkoxy group, an amino group, an alkylamino group, a methylenedioxy group, a hydroxy group, a nitro group, a nitrile group and a carboxyl group, with the number of the substituents being from 1 to 5.

Specific examples of such aryl group include a phenyl group; alkylphenyl group having an alkyl group with a carbon number of 1 to 5, such as methylphenyl and ethylphenyl; an alkoxyphenyl group having an alkoxy group with a carbon number of 1 to 5, such as methoxyphenyl and ethoxyphenyl; an alkylaminophenyl group having an alkylamino group with a carbon number of 1 to 5, such as dimethylaminophenyl and diethylaminophenyl; a halogenophenyl group such as fluorophenyl, chlorophenyl, bromophenyl and iodophenyl; a methylenedioxyphenyl group; a hydroxyphenyl group; a nitrophenyl group; a cyanophenyl group; a carboxyphenyl group and the like.

The aryl group is a substituent represented by the following general formula (IX)

(General formula (IX))

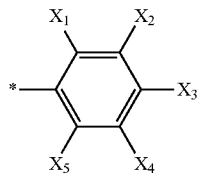

(IX)

wherein $X_1$ to $X_5$ each independently represent a group selected from the group consisting of a hydrogen atom, a halogen atom, an alkyl group, an alkoxy group, an amino group, an alkylamino group, a methylenedioxy group, a hydroxy group, a nitro group, a nitrile group, and a carboxyl group.

According to the triazolopyrimidine compound of one aspect of the present invention, R is preferably an aryl group, more preferably an aryl group having a substituent for phenyl group being a halogen atom, a nitro group or a nitrile group, in terms of cell proliferation inhibitory activities.

The 8-methyl-[1,2,4]triazolo[4,3-c]pyrimidin-5-one compound (I) and 8-methyl-[1,2,4]triazolo[1,5-c]pyrimidine-5-one compound (II) according to one aspect of the present invention include compounds having functional groups described in Scheme 1. In Scheme 1, "Me" indicates a methyl group, "Et" indicates an ethyl group, and "Ph" indicates a phenyl group. For example, 4-MeO—$C_6H_4$ indicates presence of a methoxy group at the 4-position. The same shall apply hereinafter in the present specification and the context.

Methods of synthesizing compounds according to one aspect of the present invention will be described below. 8-Methyl-[1,2,4]triazolo[4,3-c]pyrimidin-5(6H)-one compounds represented by the general formula (I), wherein substituent R is a substituent represented by a-f, s, and t described in Scheme 1, namely, compounds 4a-f, s, t, and 8-methyl-[1,2,4]triazolo[1,5-c]pyrimidine-5 (6H)-one compounds represented by the general formula (II), wherein substituent R is a substituent represented by a-t described in Scheme 1, namely, compounds 5a-t, can be synthesized according to the following reaction formula (Scheme 1), but the production methods of producing both triazolopyrimidine compounds, wherein R is an alkyl or aryl group, are not particularly limited thereto.

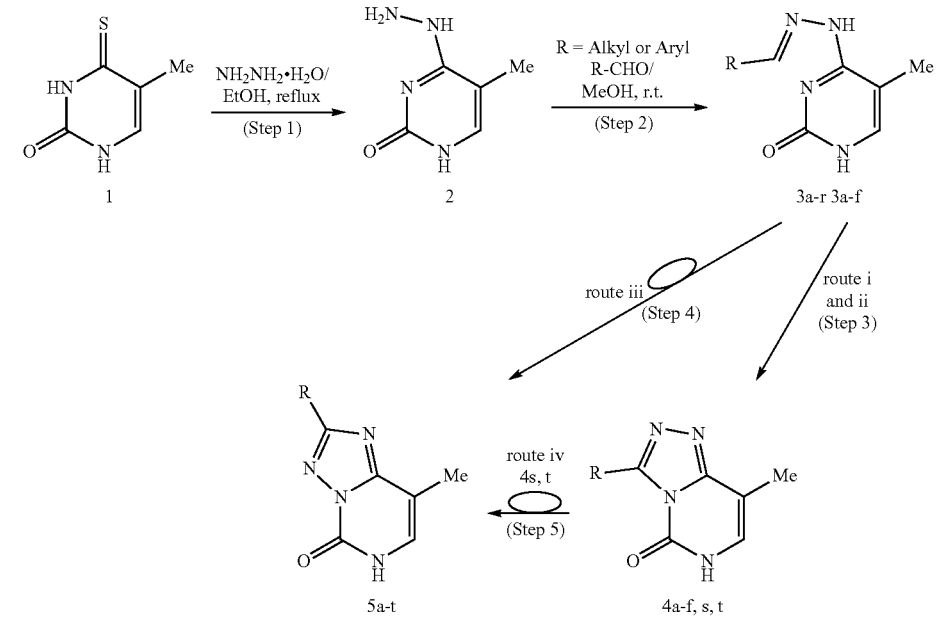

Scheme 1 route i: 70% $HNO_3$, TFA, r.t.-40° C.
route ii: Pb(OAc)$_4$, TFA, r.t.
route iii: 70% $HNO_3$, DMF, 100° C.-reflux
route iv: EtOH or DMSO, r.t.-100° C.

| Conpd 3, 4, 5 | R |
|---|---|
| a: | Et |
| b: | Ph |
| c: | 4-Me—$C_6H_4$ |
| d: | 4-MeO—$C_6H_4$ |
| e: | 2,4,6-(MeO)$_3$—$C_6H_2$ |
| f: | 4-$O_2$N—$C_6H_4$ |
| g: | 2-F—$C_6H_4$ |
| h: | 4-F—$C_6H_4$ |
| i: | 4-Cl—$C_6H_4$ |
| j: | 3,4-Cl$_2$—$C_6H_3$ |
| k: | 2-Br—$C_6H_4$ |
| l: | 4-Br—$C_6H_4$ |
| m: | 4-NC—$C_6H_4$ |
| n: | 4-HOOC—$C_6H_4$ |
| o: | 3,4-OCH$_2$O—$C_6H_3$ |
| p: | 3-Pyridyl |
| q: | 4-Pyridyl |
| r: | 2-Naphthyl |
| s: | 4-MeO-3-$O_2$N—$C_6H_3$ |
| t: | 2,4,6-(MeO)$_3$-3-$O_2$N—$C_6H$ |

In Scheme 1, R represents an ethyl group or an aryl group. In the present specification, "MeOH" indicates methanol, "EtOH" indicates ethanol, "Ac" indicates an acetyl group, "Pb(OAc)$_4$" indicates lead tetraacetate, "TFA" indicates trifluoroacetic acid, "DMF" indicates N,N-dimethylformamide, and "DMSO" indicates dimethyl sulfoxide.

Briefly, a hydrazino compound 2 shown in Scheme 1 can be obtained by subjecting a compound 1 to reaction with hydrazine hydrate while heating (Step 1). Next, aldehyde hydrazone compounds 3a-r can be obtained by reacting the compound 2 with each of various aldehydes (Step 2). Then 70% nitric acid is added to each of the compounds 3a-f in trifluoroacetic acid, and subjected to oxidation reaction at temperature in the range from room temperature (20° C.) to 40° C. (Route i) to obtain corresponding 3-substituted 8-methyl-[1,2,4]triazolo[4,3-c]pyrimidin-5(6H)-one compounds 4a-c, f, and compound 4s and 4t, respectively. The compounds 4a-c, f are ring-closed compounds, and the compounds 4s and 4t are resulted by simultaneous occurrence of nitration with ring-closure from compounds 3d and 3e. Further, each of the compounds 3b, d, e can be subjected to oxidation reaction with lead tetraacetate at room temperature (Route ii) to obtain corresponding compounds 4b, d, e, respectively, as a ring-closed compound (Step 3). On the other hand, each of the compounds 3a-r can be heated at 100° C. or under reflux in DMF to obtain 2-substituted 8-methyl-[1,2,4]triazolo[1,5-c]pyrimidin-5(6H)-one compounds 5a-r, respectively, as a rearranged compound of the compound 4 (Step 4). Furthermore, each of the compounds 4s, t before rearrangement can be heated in ethanol or DMSO to obtain corresponding compounds 5s, t, respectively, as its rearranged compound (Step 5). Oxidizing agents and solvents used in each scheme and step are not particularly limited as long as the desired compounds can be obtained, and can be selected appropriately according to the reactions in each scheme and step. Hereinafter, each step will be described.

(Step 1)

While this step was reported in the rapid publication (T. Nagamatsu, et al., *Heterocycles*, 57, No. 4, 631-636 (2002), which is incorporated by reference in its entirety.), no detailed synthesis technique has been reported yet. The compound 1 can be synthesized according to a known synthesis technique (R. N. Castle, et al., *J. Heterocycl. Chem.* 3, 79 (1966), which is incorporated by reference in its entirety.), the resulting compound 1 can be subjected to reaction with hydrazine hydrate while heating to obtain a hydrazino compound 2.

(Step 2)

Novel various aldehyde hydrazone compounds 3a-r can be prepared by the known synthesis technique (T. Nagamatsu, et al., *Heterocycles*, 57, No. 4, 631-636 (2002), which is incorporated by reference in its entirety.).

To the compound 2 (4 mmol), aldehyde represented by R—CHO (4.8 mmol) (wherein R represents an ethyl group or an aryl group) is provided and reacted in organic solvent of methanol under stirring at room temperature for 30 minutes to 2 hours to obtain compounds 3a-r, respectively.

(Step 3)

Through route i in this step, each of the compounds 3a-f can be subjected to nitric acid oxidation using 70% nitric acid as an appropriate oxidizing agent to prepare corresponding compounds 4a-c, f, respectively, as a ring-closed compound. In addition, oxidized ring-closed compounds of compounds 3d and 3e simultaneously undergo nitration by the nitric acid, resulting compounds 4s, t, respectively.

The oxidizing agent used for nitric acid oxidation is not particularly limited as long as it is an oxidizing agent capable of nitric acid oxidation, and for example, nitric acid in the range between 50% and 70% can be used, and 70% nitric acid is preferable. The oxidation reaction may be carried out in a solvent, for example, an acid solvent such as glacial acetic acid and TFA, or a mixed solvent containing them, and is preferably carried out in TFA. The reaction temperature is not particularly limited as long as it is a temperature at which a ring-closed compound can be produced by oxidation, and is preferably in the range between 20° C. and 40° C.

In addition, through route ii in Step 3, each of the compounds 3b, d, e can be oxidized with lead tetraacetate (oxidizing agent) at room temperature to prepare its corresponding compounds 4b, d, e, respectively, as a ring-closed compound. The reactions in route i and route ii, for example, can be carried out under the following conditions.

(Route i): Each 4-alkylidenehydradino-5-methylpyrimidine-2(1H)-one or 4-arylmethylidenehydradino-5-methylpyrimidine-2(1H)-one 3a-f (0.60 mmol) and 70% nitric acid (0.66 mmol) are added to TFA, and each mixture is stirred at room temperature (20° C.) to 40° C. for 30 minutes to 3 hours to obtain desired compounds 4a-c, f, s, t, respectively, in the form of colorless powder.

(Route ii): Each of 4-arylmethylidenhydrazino-5-methylpyrimidine-2(1H)-one compounds 3b, d, e (0.60 mmol) and lead tetraacetate (0.72 mmol) are added to TFA, and each mixture is stirred at room temperature (20° C.) for 30 minutes to 1 hour to obtain desired compounds 4b, d, e, respectively, in the form of colorless powder.

(Step 4)

The 2-substituted 8-methyl-[1,2,4]triazolo[1,5-c]pyrimidin-5(6H)-one compounds 5a-r as rearranged compounds of the compound 4 can be prepared by nitric acid oxidation using an oxidizing agent under the heating condition of the aldehyde hydrazone compounds 3a-r, respectively.

The oxidizing agent is not particularly limited as long as it is an oxidizing agent capable of the nitric acid oxidation, for example, nitric acid in the range between 50% and 70% can be used, and 70% nitric acid is preferable. Its solvent is not particularly limited as long as its boiling point is sufficient for the nitric acid oxidation, and is preferably DMF. For example, it can be performed under the following condition. (Route iii): Each 4-alkylidenehydradino-5-methylpyrimidine-2(1H)-one or 4-arylmethylidenehydradino-5-methylpyrimidine-2(1H)-one compounds 3a-r (1 mmol) and 70% nitric acid (1 mmol) are added to DMF, and each mixture is heated and stirred at 100° C. or under reflux for 1 hour to obtain corresponding desired compounds 5a-r, respectively.

(Step 5)

Further, each of the compounds 4s, t is heated in EtOH or DMSO to obtain compounds 5s, t, respectively, as a thermally rearranged compound. The route iv reaction in Step 5, for example, can be carried out under the following conditions. (Route iv): Each of 3-substituted 8-methyl-[1,2,4]triazolo[4,3-c]pyrimidin-5(6H)-one compounds 4s, t (0.60 mmol) is added to EtOH or DMSO, and each mixture is stirred at room temperature (20° C.) to 100° C. for 2 hours to obtain compounds 5s, t, respectively, as a rearranged compound.

The compound represented by the general formula (III) is a compound in which the oxo group at the 5-position of the triazolo[1,5-c]pyrimidine compound represented by the general formula (II) is substituted with a chloro group. The 2-substituted 5-chloro-8-methyl-[1,2,4]triazolo[1,5-c]pyrimidine compound 6 represented by the general formula (III) can be synthesized according to the following reaction formula (Scheme 2), while the production method is not particularly limited thereto.

Scheme 2

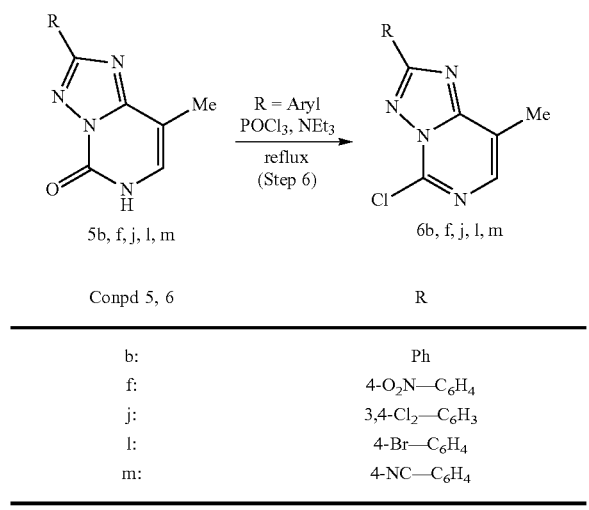

| Conpd 5, 6 | R |
|---|---|
| b: | Ph |
| f: | 4-O$_2$N—C$_6$H$_4$ |
| j: | 3,4-Cl$_2$—C$_6$H$_3$ |
| l: | 4-Br—C$_6$H$_4$ |
| m: | 4-NC—C$_6$H$_4$ |

In Scheme 2, R represents an aryl group.

In the present specification, POCl$_3$ indicates phosphorus oxychloride and NEt$_3$ indicates triethylamine.

Briefly, chloro compounds 6b, f, j, l, m can be respectively obtained by dissolving compounds 5b, f, j, l, m synthesized in Scheme 1 above in phosphorus oxychloride, and heating under reflux in the presence of triethylamine. Hereinafter, this step will be described.

(Step 6)

Each of the 2-substituted 8-methyl-[1,2,4]triazolo[1,5-c]pyrimidin-5(6H)-one compounds 5b, f, j, l, m (1.3 mmol) and triethylamine (4 mL) are added to POCl$_3$ (10 mL), the mixture is heated under reflux overnight and is added with water little by little under ice cooling to dissolve unreacted POCl$_3$, and then extracted with CH$_2$Cl$_2$ (dichloromethane) to obtain corresponding chloro compounds 6b, f, j, l, m, respectively, as colorless powdery or needle-like crystals.

On the other hand, the compound represented by the general formula (IV) is a compound in which the methyl group at the 8-position of the triazolo[1,5-c]pyrimidine compound represented by the general formula (II) is substituted with a fluorine group. The 2-substituted 8-fluoro-[1,2,4]triazolo[1,5-c]pyrimidin-5(6H)-one compound 9 represented by the general formula (IV) can be synthesized according to the following reaction formula (Scheme 3), while the production method is not particularly limited thereto.

Scheme 3

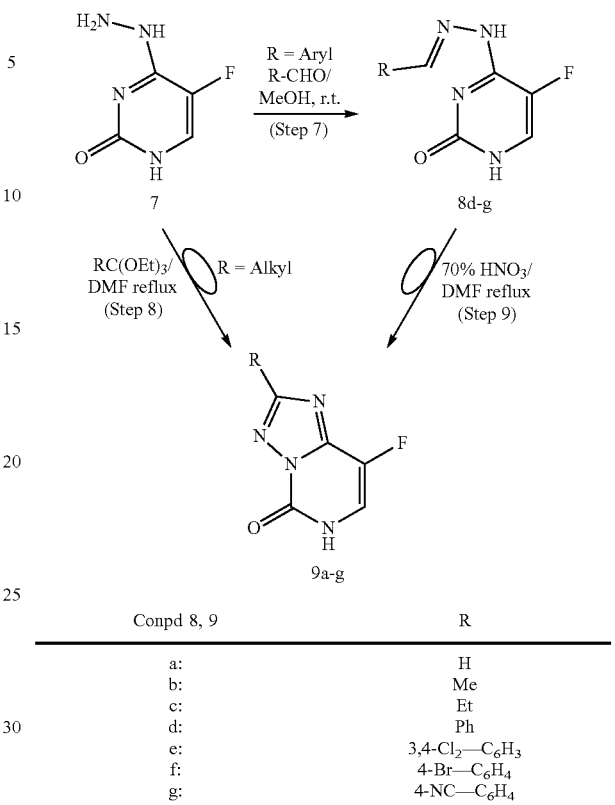

| Conpd 8, 9 | R |
|---|---|
| a: | H |
| b: | Me |
| c: | Et |
| d: | Ph |
| e: | 3,4-Cl$_2$—C$_6$H$_3$ |
| f: | 4-Br—C$_6$H$_4$ |
| g: | 4-NC—C$_6$H$_4$ |

In Scheme 3, R represents a hydrogen atom, an alkyl group or an aryl group.

In the present specification, RC(OEt)$_3$ indicates orthoester.

Briefly, a compound 7 is synthesized according to a known synthesis technique (V. Uchytilova, et al., *Collection of Czechoslovak Chem. Communications*, 40 (8), 2347 (1975), which is incorporated by reference in its entirety.), and the resulting compound 7 is reacted with each of various arylaldehydes to obtain 4-arylmethylidenehydradino-5-fluoropyrimidin-2(1H)-one compounds 8d-g, respectively (Step 7). To the hydrazino compound 7, each of orthoesters can be added in DMF, and the mixture is then heated and stirred to obtain an 8-fluoro-[1,2,4]triazolo[1,5-c]pyrimidin-5(6H)-one compound 9a or its 2-alkyl derivative compounds 9b, c, respectively (Step 8). On the other hand, 70% nitric acid (oxidizing agent) can be added to each of the aldehyde hydrazone compounds 8d-g in DMF and then heated to obtain corresponding 2-aryl-8-fluoro-[1,2,4]triazolo[1,5-c]pyrimidine-5(6H)-one compounds 9d-g, respectively, as an oxidized ring-closed rearranged compound (Step 9). Hereinafter, each step will be described.

(Step 7)

The 5-fluoro-4-hydrazinopyrimidine-2(1H)-one compound 7 (2.08 mmol) and an appropriate arylaldehyde (2.70 mmol) are added to MeOH (12 mL), and then stirred at room temperature for 2 hours to obtain corresponding aldehyde hydrazone compounds 8d-g, respectively, as colorless powdery or needle-like crystals.

(Step 8)

Orthoester used in each step is not particularly limited as long as desired compounds can be obtained, for example, orthoester having methyl or ethyl group in its alkoxy group can be used. Step 8 can be carried out under the following conditions, for example. The 5-fluoro-4-hydrazinopyrimidine-2(1H)-one compound 7 (1.39 mmol) and an appropriate triethyl orthoester (1.81 mmol) are added to DMF (10 mL), and the mixture is heated under reflux for 1 hour. After the reaction, the solvent is distilled off under reduced pressure to obtain corresponding desired compounds 9a-c, respectively, as colorless powdery or needle-like crystals.
(Step 9)

The 4-arylmethylidenhydrazino-5-fluoropyrimidine-2 (1H)-one compound 8d-g (0.80 mmol) and 70% nitric acid (1.10 mmol) are added to DMF (6 mL), and the mixture is heated under reflux for 2 hours. After the reaction, the solvent is distilled off under reduced pressure to obtain corresponding desired compounds 9d-g, respectively, as colorless powdery or needle-like crystals.

Further, the compound represented by the general formula (V) is a 3-substituted 8-methyl-[1,2,4]triazolo[4,3-c]pyrimidine-5(6H)-thione compound in which the oxo group at the 5-position in the triazolo[4,3-c]pyrimidine compound represented by the general formula (I) is substituted with a thioxo group. In addition, the compound represented by the general formula (VI) is a 2-substituted 8-methyl-[1,2,4]triazolo[1,5-c]pyrimidine-5(6H)-thione compound in which the oxo group at the 5-position in the triazolo[1,5-c]pyrimidine compound represented by the general formula (II) is substituted with a thioxo group. Of the general formula (V), compounds 13a, b, wherein substituent R is a substituent represented by a and b described in Scheme 4, and of the general formula (VI), compounds 14a-c, wherein substituent R is a substituent represented by a to c described in Scheme 4 can be synthesized according to the following reaction formula (Scheme 4), while the production method is not particularly limited thereto.

In Scheme 4, R represents a hydrogen atom, a methyl group or a phenyl group.

First, a 5-methylpyrimidine-2,4(1H,3H)-dithione compound 10 as starting material can be synthesized by the known synthesis technique (R. N. Castle, et al., *J. Heterocycl. Chem.*, 3, 79 (1966), which is incorporated by reference in its entirety.), the resulting compound 10 in ethanol is added with water-containing hydrazine and heated under reflux to obtain a 4-hydrazino-5-methylpyrimidine-2(1H)-thione compound 11 (Step 10). Next, each of aldehydes is reacted with this compound in methanol to obtain a 4-aldehyde hydrazone compound 12b or 12c of the 5-methylpyrimidine-2(1H)-thione compound (Step 11). Then, the hydrazino compound 11 is dissolved in TFA, added with triethyl orthoformate and carried out oxidation reaction at room temperature to obtain a [1,2,4]triazolo[4,3-c]pyrimidin-5(6H)-thione compound 13a (Step 12). Further, the aldehyde hydrazone compound 12b is dissolved in TFA, added with lead tetraacetate and oxidized at room temperature to obtain a 3,8-dimethyl-[1,2,4]triazolo[4,3-c]pyrimidin-5(6H)-thione compound 13b (Step 13). On the other hand, the hydrazino compound 11 is dissolved in DMF, added with each of triethyl orthoesters, and heated under reflux to obtain an 8-methyl-[1,2,4]triazolo[1,5-c]pyrimidin-5(6H)-thione compound 14a as a rearranged compound or its 2-position substituted derivative compounds 14b, c (Step 14). Hereinafter, each step will be described.
(Step 10)

The 5-methylpyrimidine-2,4(1H,3H)-dithione 10 (12.64 mmol) and hydrazine hydrate (31.96 mmol) are added to EtOH (16 mL), and the mixture is heated under reflux for 10 minutes. After the reaction, the precipitated crystals are collected by filtration and recrystallized from water to obtain a compound 11 as colorless powdery crystals.

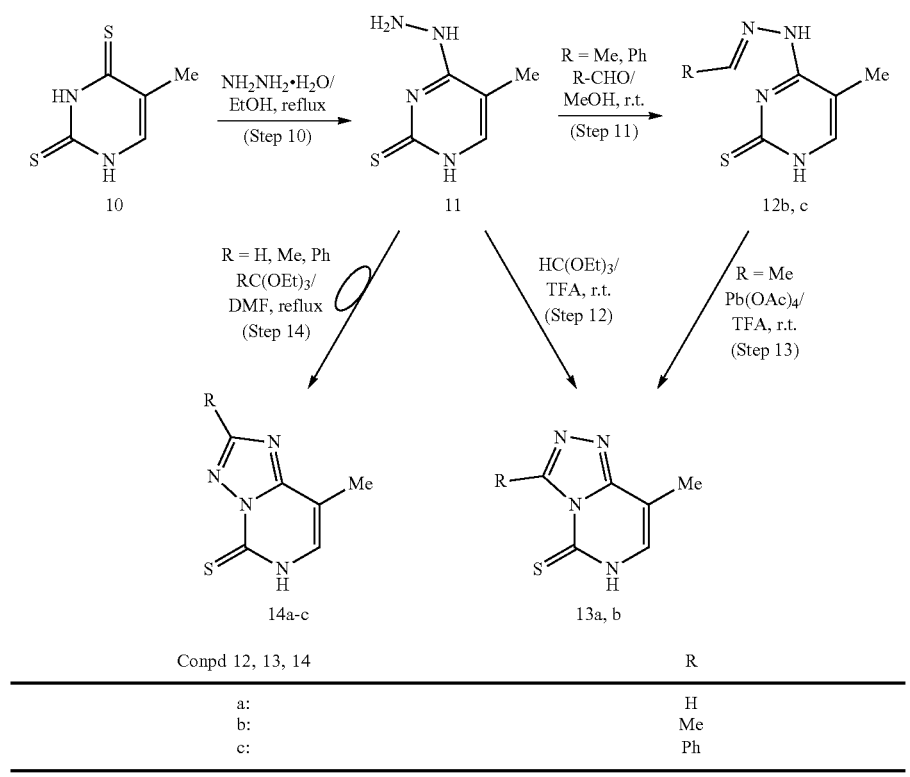

Scheme 4

| Conpd 12, 13, 14 | R |
|---|---|
| a: | H |
| b: | Me |
| c: | Ph |

(Step 11)

The 4-hydrazino-5-methylpyrimidine-2(1H)-thione compound 11 (3 mmol) and each of aldehydes (3.6 mmol) are added to MeOH (15 mL), each mixture is stirred at room temperature for 1 to 12 hours, and the precipitated crystals are collected by filtration and then recrystallized from EtOH to obtain a corresponding aldehyde hydrazone compound 12b or c.

(Step 12)

The 4-hydrazino-5-methylpyrimidine-2(1H)-thione compound 11 (1 mmol) and triethyl orthoformate (5 mmol) are added to TFA (6 mL), the mixture is stirred at room temperature for 30 minutes, and the solvent is distilled off under reduced pressure. The residue can be recrystallized from ethanol to obtain a corresponding 8-methyl-[1,2,4]triazolo[4,3-c]pyrimidine-5(6H)-thione compound 13a.

(Step 13)

The 4-ethylidenehydrazino-5-methylpyrimidin-2(1H)-thione compound 12b (0.6 mmol) and lead tetraacetate (0.60 mmol) are added to TFA (3 mL), each mixture is stirred for 10 minutes at room temperature, the solvent is distilled off under reduced pressure, and the residue is recrystallized from ethanol to obtain a corresponding 3,8-dimethyl-[1,2,4]triazolo[4,3-c]pyrimidine-5(6H)-thione compound 13b as colorless powdery crystals.

(Step 14)

The 4-hydrazino-5-methylpyrimidine-2(1H)-thione compound 11 (2 mmol) and each of triethyl orthoesters (2.4 mmol) are added to DMF (15 mL), and each mixture is heated under reflux for 0.5 to 2 hours, the solvent is distilled off under reduced pressure, and the residue is recrystallized from EtOH to obtain a corresponding 8-methyl-[1,2,4]triazolo[1,5-c]pyrimidin-5(6H)-thione compound 14a or its 2-position substituted compounds 14b, c.

Further, the compound represented by the general formula (VII) is a 3-substituted 8-methyl-[1,2,4]triazolo[4,3-c]pyrimidin-5-amine compound in which the oxo group at the 5-position in the triazolo[4,3-c]pyrimidine compound represented by the general formula (I) is substituted with the amino group. Furthermore, the compound represented by the general formula (VIII) is a 2-substituted 8-methyl-[1,2,4]triazolo[1,5-c]pyrimidine-5-amine compound in which the oxo group at the 5-position in the triazolo[1,5-c]pyrimidine compound represented by the general formula (II) is substituted with amino group. Of the general formula (VII), compounds 19a-c, wherein substituent R is a substituent represented by a to c described in Scheme 5, and of the general formula (VIII), compounds 20a-c, wherein substituent R is a substituent represented by a to c described in Scheme 5, can be synthesized according to the following reaction formula (Scheme 5), while the production method is not particularly limited thereto.

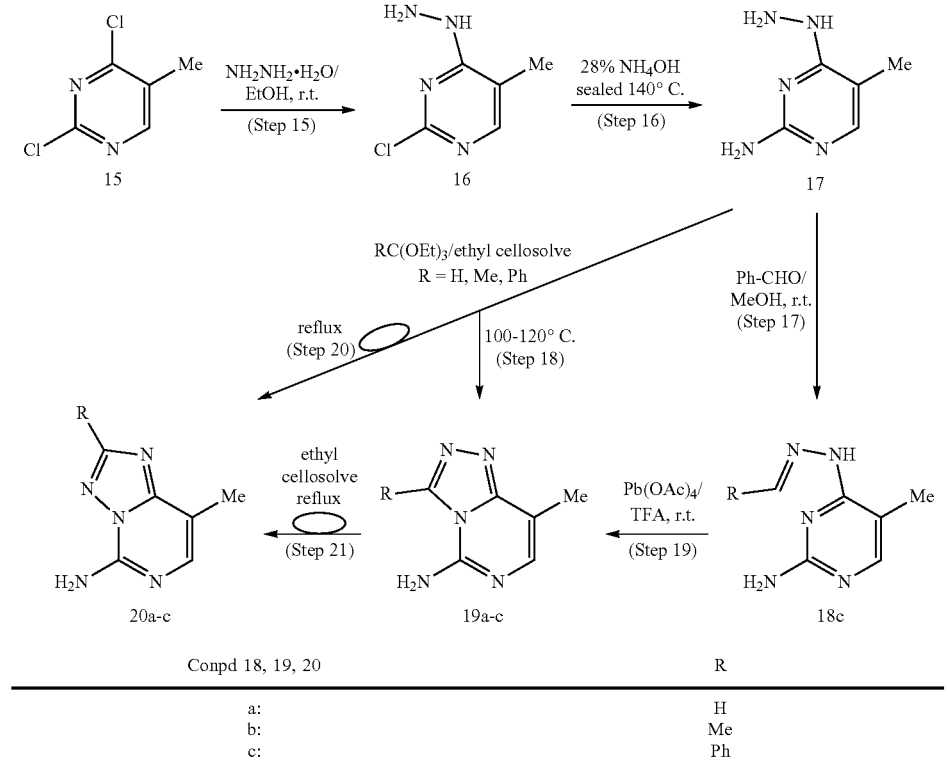

Scheme 5

| Conpd 18, 19, 20 | R |
|---|---|
| a: | H |
| b: | Me |
| c: | Ph |

In Scheme 5, R represents a hydrogen atom, a methyl group or a phenyl group.

First, a 2,4-dichloro-5-methylpyrimidine compound 15 as starting material can be synthesized by a known synthesis technique (H. C. Koppel, et al., *J. Org. Chem.*, 27, 181 (1962), which is incorporated by reference in its entirety.), the resulting compound 15 dissolved in ethanol is added with water-containing hydrazine and reacted while stirring at room temperature to obtain a 2-chloro-4-hydrazino-5-methylpyrimidine compound 16, in which the 4-position in the compound 15 only is hydrazinolated (Step 15). Next, aqueous ammonia is added to the compound 16, and the mixture is subjected to reaction while heating in a sealed tube to obtain a 2-amino-4-hydrazino-5-methylpyrimidine compound 17, in which the 2-position in the compound 16 is aminated (Step 16). To the resulting compound 17 in this step, benzaldehyde is added at room temperature and reacted in methanol to obtain a corresponding 2-amino-4-benzylidenehydrazino-5-methylpyrimidine compound 18c (Step 17). The compound 17 can also be reacted with each of triethyl orthoesters at 100° C. to 120° C. in ethyl cellosolve to obtain a corresponding 8-methyl-[1,2,4]triazolo[4,3-c]pyrimidin-5-amine compound 19a, or its 3-position substituted derivative compounds 19b, c (Step 18). Further, lead tetraacetate is added to the aldehyde hydrazone compound 18c in TFA and reacted at room temperature to obtain a compound 19c as its oxidized ring-closed compound (Step 19). On the other hand, in the same reaction as in Step 18, triethyl orthoester is added to the hydrazino compound 17 in ethyl cellosolve, and heated under reflux to obtain an 8-methyl-[1,2,4]triazolo[1,5-c]pyrimidine-5-amine compound 20a or its 2-position substituted derivative compounds 20b, c (Step 20). In addition, each of the compounds 20a-c can be obtained by heating the compounds 19a-c under reflux in ethyl cellosolve, or subjecting them to thermal rearrangement reaction (Step 21). Hereinafter, each step will be described.

(Step 15)

Hydrazine hydrate (20.6 mmol) is added dropwise to a mixture of EtOH (4 mL) and the 2,4-dichloro-5-methylpyrimidine compound 15 (6.13 mmol) under ice-cooling, the mixture is stirred at room temperature for 10 minutes and then recrystallized from EtOH to obtain a compound 16 as needle-like crystals.

(Step 16)

The 2-chloro-4-hydrazino-5-methylpyrimidine compound 16 (6.92 mmol) is added to a 28% aqueous ammonia solution (50 mL), the mixture is heated at 140° C. for 84 hours in a sealed tube under argon atmosphere, and treated with a small amount of EtOH, resulting solid precipitate. This resulting solid is dissolved in water, then subjected to an ion exchange resin (Dowex SAR, 20-50 mesh, Cl form), and recrystallized from EtOH to obtain compound 17 as colorless needle-like crystals.

(Step 17)

The 2-amino-4-hydrazino-5-methylpyrimidine compound 17 (2 mmol) and benzaldehyde (2.4 mmol) are added to MeOH (10 mL), the mixture is stirred at room temperature for 12 hours, and the precipitated crystals are recrystallized from EtOH to obtain a corresponding aldehyde hydrazone compound 18c as colorless powdery crystals.

(Step 18)

The 2-amino-4-hydrazino-5-methylpyrimidine compound 17 (2 mmol) and each corresponding triethyl orthoester (4 mmol) are added to ethyl cellosolve (10 mL), and each mixture is heated and stirred at 100° C. to 120° C. for 30 minutes to 2.5 hours. The solvent is distilled off under reduced pressure, and the residue is treated with AcOEt (ethyl acetate), resulting precipitated crystals. The precipitated crystals can be subjected to activated carbon treatment and recrystallization in EtOH to obtain corresponding compounds 19a-c, respectively, as a ring-closed compound.

(Step 19)

The 2-amino-4-benzilidenhydrazino-5-methylpyrimidine compound 18c (1 mmol) and lead tetraacetate (1 mmol) are added to TFA (4 mL), and the mixture is stirred at room temperature for 15 to 30 minutes. The solvent is distilled off under reduced pressure. The remaining residue is then purified by silica gel column chromatography (Kieselgel 70-230 mesh), and the solid collected from the AcOEt elution fraction is recrystallized from AcOEt to obtain a corresponding 8-methyl-3-phenyl-[1,2,4]triazolo[4,3-c]pyrimidin-5-amine compound 19c.

(Step 20)

The 2-amino-4-hydrazino-5-methylpyrimidine compound 17 (2 mmol) and each of triethyl orthoesters (3 mmol) are added to ethyl cellosolve (20 mL), and each mixture is heated under reflux for 0.5 to 32 hours. After solvent distillation, the residue is treated with AcOEt to precipitate crystals. The precipitated crystals is recrystallized from EtOH to obtain an 8-methyl-[1,2,4]triazolo[1,5-c]pyrimidin-5-amine compound 20a as a rearranged compound or its 2-position substituted compounds 20b, c, which are corresponded with compounds 19a-c, respectively.

(Step 21)

Each of the 8-methyl-[1,2,4]triazolo[4,3-c]pyrimidine compounds 19a-c (2 mmol) is added to ethyl cellosolve (10 mL), and the mixture is heated under reflux for 12 hours. After the reaction, the solvent is distilled off under reduced pressure and the residue is treated with AcOEt to precipitate crystals. The precipitated crystals can be recrystallized from EtOH to obtain corresponding compounds 20a-c, respectively, as a rearranged compound.

The triazolopyrimidine compounds (I) to (VIII) of the present invention and synthesis intermediates may be isolated/purified by standard isolation/purification means for nucleobases: for example, recrystallization and various chromatography techniques may be used for isolation/purification.

The triazolopyrimidine compounds (I) to (VIII) of the present invention may be any of a free form, a salt or a hydrate (including a hydrate salt). Examples of the salt include salts of inorganic acids, such as hydrochloride, sulfate and hydrobromide, salts of organic acids, such as oxalate, citrate and malate, or ammonium salts. In particular, pharmaceutically acceptable salts are preferred.

The triazolopyrimidine compounds of the present invention and a composition containing the foregoing compound are useful as a therapeutic agent for malignant tumors. The tumors include cancer, sarcoma, hematological tumors and the like, and examples of them include: gastric cancer, liver cancer, colon/rectal cancer, breast cancer, pancreatic cancer, cervical cancer, endometrial cancer and ovarian cancer, esophageal cancer, lung cancer, leukemia, myeloma, malignant lymphoma and head and neck tumors. The triazolopyrimidine compounds of the present invention and a composition containing the foregoing compound are useful as a therapeutic agent for the above-mentioned various cancer diseases. Administration to human may be via any route such as oral, enteral, parenteral (intravenous injection, intravenous drip infusion), and external use (ointment) for treating the above-described diseases. While the dose may be suitably determined depending on the age, condition and body weight of the patients, it is typically chosen from a range between 1 and 100 mg/kg body weight per day and is administered in a single dose or multiple doses.

When used as a medical drug, the compound of the present invention is preferably used as a composition containing a pharmaceutically acceptable carrier, such as excipient agent and other additive agent. Examples of carriers include solid carriers, such as lactose, kaolin, sucrose, crystalline cellulose, corn starch, talc, agar, pectin, stearic acid, magnesium stearate, lecithin, and sodium chloride; and liquid carriers, such as glycerin, peanut oil, polyvinylpyrrolidone, olive oil, ethanol, benzyl alcohol, propylene glycol, and water.

The pharmaceutical composition may take any dosage form: examples include tablets, powders, granules, and capsules for solid carriers, and syrups, emulsions, creams, gels, pastes, and injections for liquid carriers.

EXAMPLES

The present invention will now be described more specifically with reference to Examples, which are not intended to limit the present invention in any way.

Example 1. Synthesis Examples of 3-substituted 8-methyl-[1,2,4]triazolo[4,3-c]pyrimidin-5(6H)-one compounds 4a-f, s, t (General formula I) and 2-substituted 8-methyl-[1,2,4]triazolo[1,5-c]pyrimidin-5(6H)-one compounds 5a-t (General formula II)

According to the reaction formula described in Scheme 1 described above, triazolopyrimidine compounds represented by compounds 4a-f, s, t, and 5a-t were synthesized.

Synthesis Example 1: Synthesis of 4-hydrazino-5-methylpyrimidin-2(1H)-one compound 2

A 4-thiothymine compound 1 (1 g, 7.0 mmol) and hydrazine hydrate (2 g, 40 mmol) were added to EtOH (8 mL), and the mixture was heated under reflux for 10 minutes. After the reaction, the precipitated crystals were collected by filtration. The collected crystals were recrystallized from water to obtain colorless needle-like crystals (0.80 g, 81%, mp>300° C.).
$^1$H NMR [200 MHz, (CD$_3$)$_2$SO]δ: 1.68 (3H, s, 5-Me), 5.82 (2H, br s, exchangeable with D$_2$O, NH$_2$), 6.68 (1H, br s, exchangeable with D$_2$O, 6-H), 9.41 (2H, br, exchangeable with D$_2$O, NH); IR: 3260 ($v_{as}$, NH$_2$), 3180 ($v_s$, NH$_2$), 3130, 3060 (v, NH), 1660 (v, C=O), 1600 cm$^{-1}$ (δ, NH$_2$); Anal. Calcd. for C$_5$H$_8$N$_4$O.½H$_2$O: C, 40.26; H, 6.08; N, 37.56 Found: C, 39.97; H, 5.96; N, 37.73; MS (FAB, glycerol matrix): m/z=141 (MH$^+$).

Synthesis Example 2: General synthesis of 4-alkylidenehydradino-5-methylpyrimidine-2(1H)-one and 4-arylmethylidenehydrazino-5-methylpyrimidin-2(1H)-one compounds 3a-r The 4-hydrazino-5-methylpyrimidine-2(1H)-one compound 2 (4 mmol) and each of aldehydes (4.8 mmol) were added to MeOH (25 mL), and each mixture was stirred at room temperature for 30 minutes to 2 hours. After the reaction, the precipitated crystals were collected by filtration, and the collected crystals were recrystallized from EtOH to obtain corresponding desired compounds 3a-r, respectively (Tables 1 to 4).

Synthesis Example 3: General synthesis of 3-substituted 8-methyl-[1,2,4]triazolo[4,3-c]pyrimidine-5(6H)-one compounds 4a-f, s, t (Route i): Each of 4-alkylidenehydrazino-5-methylpyrimidine-2(1H)-one or 4-arylmethylidenehydrazino-5-methylpyrimidine-2(1H)-one compounds 3a-f (0.60 mmol) and 70% nitric acid (0.06 mL, 0.66 mmol) were added to TFA (3 mL), and each mixture was stirred at room temperature (20° C.) or at 40° C. for 30 minutes to 3 hours. After the reaction, the solvent is removed by evaporation under reduced pressure. After treatment with diethyl ether, the resulting precipitated solid was collected by filtration. The collected solid was washed in 0.5% aq. KHCO$_3$ to obtain corresponding desired compounds 4a-c, f, s, t, respectively, in the form of colorless powder (Tables 5 and 6).

(Route ii): Each of 4-arylmethylidenhydrazino-5-methylpyrimidine-2(1H)-one compounds 3b, d, e (0.60 mmol) and lead tetraacetate (0.72 mmol) were added to TFA (3 mL), and each mixture was stirred at room temperature (20° C.) for 30 minutes to 1 hour. After the reaction, the solvent is removed by evaporation under reduced pressure. After treatment with AcOEt, the resulting precipitated solid was collected by filtration. The collected solid was washed with an aqueous solution of 0.5% potassium hydrogen carbonate to obtain desired compounds 4b, d, e, respectively, in the form of colorless powder (Tables 5 and 6).

Synthesis Example 4: Synthesis of 2-substituted 8-methyl[1,2,4]triazolo[1,5-c]pyrimidin-5(6H)-one compounds 5a-t (Route iii): Each of 4-alkylidenehydrazino-5-methylpyrimidine-2(1H)-one or 4-arylmethylidenehydrazino-5-methylpyrimidine-2(1H)-one compounds 3a-r (1 mmol) and 70% nitric acid (0.1 mL, 1.1 mmol) were added to DMF (10 mL), and each mixture was heated and stirred at 100° C. or under reflux for 1 hour. After the reaction, the solvent is removed by evaporation under reduced pressure, followed by treating with AcOEt, and the resulting precipitated solid was then collected by filtration. This resulting solid was recrystallized from EtOH to obtain corresponding desired compounds 5a-r, respectively (Tables 7 to 10).

(Route iv): Each of 3-substituted 8-methyl-[1,2,4]triazolo[4,3-c]pyrimidin-5(6H)-one compounds 4s, t (0.60 mmol) was added to EtOH (20 mL) or DMSO (10 mL), and each mixture was stirred for 2 hours at room temperature (20° C.) to 100° C. After the reaction, the solvent is removed by evaporation under reduced pressure, followed by treating with AcOEt, and the resulting precipitated solid was collected by filtration. This resulting solid was recrystallized from EtOH to obtain corresponding rearranged compounds 5s, t, respectively (Tables 8 and 10).

Example 2. Synthesis Examples of 2-substituted 5-chloro-8-methyl-[1,2,4]triazolo[1,5-c]pyrimidine compounds (6b, f, j, l, m) (General formula III)

Triazolopyrimidine compounds represented by the compounds 6b, f, j, l, m were respectively synthesized according to the reaction formula described in Scheme 2 described above.

Synthesis Example 5: General synthesis of 2-substituted 5-chloro-8-methyl-[1,2,4]triazolo[1,5-c]pyrimidine compounds 6b, f, j, l, m Each of 2-substituted 8-methyl-[1,2,4]triazolo[1,5-c]pyrimidine-5(6H)-one compounds 5b, f, j, l, m (1.3 mmol) and triethylamine (4 mL) were added to POCl$_3$ (10 mL), and each mixture was heated under reflux overnight. After the reaction, water was added to the solution little by little under ice-cooling to decompose unreacted POCl$_3$. After extraction with CH$_2$Cl$_2$, the solvent is removed by evaporation under reduced pressure, the resulting precipitated crystals were added with a small amount of EtOH and then collected by filtration to obtain corresponding desired compounds 6b, f, j, l, m, respectively, as colorless powdery or needle-like crystals (Tables 11 and 12).

Example 3. Synthesis Examples of 2-substituted 8-fluoro-[1,2,4]triazolo[1,5-c]pyrimidine-5(6H)-one compounds 9a-g (General formula IV)

Triazolopyrimidine compounds represented by the compounds 9a-g were respectively synthesized according to the reaction formula described in Scheme 3 described above.

Synthesis Example 6: General synthesis of 4-arylmethylidenhydrazino-5-fluoropyrimidine-2(1H)-one compounds 8d-g The 5-fluoro-4-hydrazinopyrimidine-2(1H)-one compound 7 (0.30 g, 2.08 mmol) and an appropriate aryl aldehyde (2.70 mmol) were added to MeOH (12 mL), and the mixture was stirred at room temperature for 2 hours. After the reaction, the precipitated crystals were collected by filtration and washed with diethyl ether. The resulting crystals were recrystallized from EtOH to obtain corresponding desired compounds 8d-g, respectively, as colorless powdery or needle-like crystals (Tables 13 and 14).

Synthesis Example 7: General synthesis of 8-fluoro-[1,2,4]triazolo[1,5-c]pyrimidin-5(6H)-one compound 9a and its 2-position alkyl-substituted derivative compounds 9b, c The 5-fluoro-4-hydrazinopyrimidine-2(1H)-one compound 7 (0.20 g, 1.39 mmol) and an appropriate triethyl orthoester (1.81 mmol) were added to DMF (10 mL), and the mixture was heated under reflux for 1 hour. After the reaction, the solvent is removed by evaporation under reduced pressure, followed by treating with AcOEt, and the resulting precipitated solid was collected by filtration. This collected solid was recrystallized from EtOH to obtain corresponding desired compounds 9a-c, respectively, as colorless powdery or needle-like crystals (Tables 15 and 16).

Synthesis Example 8: General synthesis of 2-aryl-8-fluoro-[1,2,4]triazolo[1,5-c]pyrimidine-5(6H)-one compounds 9d-g Each of 4-arylmethylidenhydrazino-5-fluoropyrimidine-2(1H)-one compounds 8d-g (0.80 mmol) and 70% nitric acid (0.1 ml, 1.10 mmol) were added to DMF (6 mL), and each mixture was heated under reflux for 2 hours. After the reaction, the solvent is removed by evaporation under reduced pressure, followed by treating with AcOEt, and the resulting precipitated solid was collected by filtration. This collected solid was recrystallized from EtOH to obtain corresponding desired compounds 9d-g, respectively, as colorless powdery or needle-like crystals (Tables 15 and 16).

Example 4. Synthesis Examples of 3-substituted 8-methyl-[1,2,4]triazolo[4,3-c]pyrimidine-5(6H)-thione compounds 13a, b (General formula V) and 2-substituted 8-methyl-[1,2,4]triazolo[1,5-c]pyrimidine-5(6H)-thione compounds 14a-c (General formula VI)

Triazolopyrimidine compounds represented by the compounds 13a, b and 14a-c were respectively synthesized according to the reaction formula described in Scheme 4 described above.

Synthesis Example 9: Synthesis of 4-hydrazino-5-methylpyrimidine-2(1H)-thione compound 11

The 5-methylpyrimidine-2,4(1H,3H)-dithione compound 10 (2.0 g, 12.64 mmol) and hydrazine hydrate (1.6 g, 31.96 mmol) were added to EtOH (16 mL), and the mixture was heated under reflux for 10 minutes. After the reaction, the precipitated crystals were collected by filtration. The collected crystals were recrystallized from water to obtain colorless powdery crystals (1.5 g, 76%, mp>257° C.).
$^1$H NMR [200 MHz, (CD$_3$)$_2$SO] δ: 1.79 (3H, s, 5-Me), 5.70 (2H, br s, exchangeable with D$_2$O, NH$_2$), 7.05 (1H, s, 6-H), 11.75 (2H, br s, exchangeable with D$_2$O, NH); IR: 3285 ($v_{as}$, NH$_2$), 3170 ($v_s$, NH$_2$), 3140, 3050 (v, NH), 1630 (δ, NH$_2$); Anal. Calcd. for C$_5$H$_8$N$_4$S: C, 38.44; H, 5.16; N, 35.87 Found: C, 38.19; H, 5.26; N, 36.12; MS (FAB, glycerol matrix): m/z=157 (MH$^+$).

Synthesis Example 10: General synthesis of 4-ethylidenehydradino-5-methylpyrimidine-2(1H)-thione and 4-benzylidenehydradino-5-methylpyrimidine-2(1H)-thione compounds 12b, c The 4-hydrazino-5-methylpyrimidine-2(1H)-thione compound 11 (0.57 g, 3 mmol) and each of aldehydes (3.6 mmol) were added to MeOH (15 mL), and each mixture was stirred at room temperature for 1 to 12 hours. After the reaction, the precipitated crystals were collected by filtration. This collected crystals were recrystallized from EtOH to obtain corresponding desired compounds 12b, c, respectively (Tables 17 and 18).

Synthesis Example 11: Synthesis of 8-methyl-[1,2,4]triazolo[4,3-c]pyrimidin-5(6H)-thione compound 13a The 4-hydrazino-5-methylpyrimidine-2(1H)-thione 11 (0.156 g, 1 mmol) and triethyl orthoformate (5 mmol) were added to TFA (6 mL), and the mixture was stirred at room temperature for 30 minutes. After the reaction, the solvent is removed by evaporation under reduced pressure, followed by treatment with diethyl ether, the precipitated crystals were then collected by filtration. The collected crystals were washed with 1% aq. KHCO$_3$, followed by recrystallization from ethanol to obtain a corresponding desired compound 13a (Tables 17 and 18).

Synthesis Example 12: Synthesis of 3,8-dimethyl-[1,2,4]triazolo[4,3-c]pyrimidine-5(6H)-thione compound 13b The 4-ethylidenehydrazino-5-methylpyrimidine-2(1H)-thione compound 12b (0.11 g, 0.6 mmol) and lead tetraacetate (0.27 g, 0.60 mmol) were added to TFA (3 mL), the mixture was stirred at room temperature for 10 minutes. After the reaction, the solvent is removed by evaporation under reduced pressure, and the residue was washed with diethyl ether, followed by treatment with EtOH to precipitate solid. The solid was collected by filtration. This collected solid was washed with 0.5% aq. KHCO$_3$ and recrystallized from ethanol to obtain a corresponding compound 13b as colorless powdery crystals (Tables 17 and 18).

Synthesis Example 13: General synthesis of 8-methyl-[1,2,4]triazolo[1,5-c]pyrimidin-5(6H)-thione compound 14a and its 2-position substituted derivative compounds 14 b, c The 4-hydrazino-5-methylpyrimidine-2(1H)-thione 11 (0.31 g, 2 mmol) and each of triethyl orthoesters (2.4 mmol)

were added to DMF (15 mL), and each mixture was heated under reflux for 30 minutes to 2 hours. After the reaction, the solvent is removed by evaporation under reduced pressure, followed by treatment with EtOH, the resulting precipitated crystals were collected by filtration. This collected crystals were recrystallized from EtOH to obtain corresponding desired compounds 14a-c, respectively, (Tables 17 and 18).

Example 5. Synthesis Examples of 3-substituted 8-methyl-[1,2,4]triazolo[4,3-c]pyrimidine-5-amine compounds (19a-c) (General formula VII) and 2-substituted 8-methyl-[1,2,4]triazolo[1,5-c]pyrimidine-5-amine compounds (20a-c) (General formula VIII)

Triazolopyrimidine compounds represented by the compounds 13a, b and 14a-c were respectively synthesized according to the reaction formula described in Scheme 5 described above.

Synthesis Example 14: Synthesis of 2-chloro-4-hydrazino-5-methylpyrimidine compound 16

Hydrazine hydrate (1 mL, 20.6 mmol) under ice-cooling was added dropwise to a mixture of EtOH (4 mL) and 2,4-dichloro-5-methylpyrimidine 15 (1.0 g, 6.13 mmol), and the mixture was stirred for 10 minutes at room temperature. After the reaction, the precipitated crystals were collected by filtration, and recrystallized from EtOH to obtain colorless needle-like crystals (0.70 g, 72%, mp>340° C.).
$^1$H-NMR [60 MHz, $(CD_3)_2SO$] δ: 1.92 (3H, s, Me), 4.58 (2H, br s, exchangeable with $D_2O$, $NH_2$), 7.74 (1H, s, 6-H), 8.59 (1H, br s, exchangeable with $D_2O$, NH); IR: 3260 ($v_{as}$, $NH_2$), 3160 ($v_s$, $NH_2$), 3050 (v, NH), 1590 cm$^{-1}$ (δ, $NH_2$); Anal. Calcd. for $C_5H_7ClN_4$: C, 37.87; H, 4.45; N, 35.33 Found: C, 37.89; H, 4.49; N, 35.55; MS (FAB, glycerol matrix): m/z=159 (MH$^+$), 161 (MH$^+$+2).

Synthesis Example 15: Synthesis of 2-amino-4-hydrazino-5-methylpyrimidine compound 17

The 2-chloro-4-hydrazino-5-methylpyrimidine 16 (1.0 g, 6.92 mmol) was added to 28% aq. $NH_3$ (50 mL), and the mixture was heated in a sealed tube under an argon atmosphere at 140° C. for hours. After the reaction, the solvent is removed by evaporation under reduced pressure, followed by treatment with a small amount of EtOH to precipitate a solid. This precipitated solid was collected by filtration, then dissolved in water, and subjected to an ion exchange resin (Dowex SAR, 20-50 mesh, Cl form, 10 g). The obtained solid was recrystallized from EtOH to obtain colorless needle-like crystals (0.30 g, 31%, mp 239° C. to 240° C.).
$^1$H NMR [200 MHz, $(CD_3)_2SO$]δ: 1.79 (3H, s, Me), 4.21 (2H, br s, exchangeable with $D_2O$, $NHNH_2$), 5.76 (2H, br s, exchangeable with $D_2O$, $NH_2$), 7.41 (1H, s, 6-H), 7.65 (1H, br s, exchangeable with $D_2O$, $NHNH_2$); IR: 3370 ($v_{as}$, $NH_2$), 3280 ($v_s$, $NH_2$), 3170 ($v_{as}$, $NH_2$), 3130 ($v_s$, $NH_2$), 3070 (v, NH), 1640 cm$^{-1}$ (δ, $NH_2$); Anal. Calcd. for $C_5H_9N_5$: C, 43.15; H, 6.52; N, 50.33 Found: C, 42.86; H, 6.37; N, 50.61; MS (FAB, glycerol matrix): m/z=140 (MH$^+$).

Synthesis Example 16: Synthesis of 2-amino-4-benzylidenehydrazino-5-methylpyrimidine compound 18c The 2-amino-4-hydrazino-5-methylpyrimidine 17 (0.28 g, 2 mmol) and benzaldehyde (0.26 g, 2.4 mmol) were added to MeOH (10 mL), and the mixture was stirred at room temperature for 12 hours. After the reaction, the precipitated crystals were collected by filtration and recrystallized from EtOH to obtain a corresponding compound 18c (0.36 g, 79%, mp 204° C.) as colorless powdery crystals.
$^1$H NMR [200 MHz, $(CD_3)_2SO$]δ: 2.10 (3H, s, 5-Me), 5.97 (2H, br s, exchangeable with $D_2O$, $NH_2$), 7.29-7.52 (3H, m, Ph-m, pH), 7.60-7.77 (2H, m, Ph-oH), 7.70 (1H, s, 6-H), 8.22 (1H, s, Ph-CH), 10.28 (1H, br s, exchangeable with $D_2O$, NH); IR: 3316 ($v_{as}$ $NH_2$), 3250 ($v_s$ $NH_2$), 1638 cm$^{-1}$ (δ $NH_2$); Anal. Calcd. for $C_{12}H_{13}N_5$: C, 63.42; H, 5.77; N, 30.82 Found: C, 63.36; H, 5.88; N, 30.52; MS (FAB, glycerol matrix): m/z=228 (MH$^+$).

Synthesis Example 17: General synthesis of 8-methyl-[1,2,4]triazolo[4,3-c]pyrimidin-5-amine compound 19a and its 3-position substituted derivative compounds 19 b, c (Route i): Corresponding 2-amino-4-hydrazino-5-methylpyrimidine (0.28 g, 2 mmol) and each of corresponding triethyl orthoesters (4 mmol) were added to ethyl cellosolve (10 mL), and each mixture was heated and stirred at 100° C. to 120° C. for 30 minutes to 2.5 hours. After the reaction, the solvent is removed by evaporation under reduced pressure, followed by treatment with AcOEt to precipitate crystals. The precipitated crystals were collected by filtration, then treated with activated carbon and recrystallized in EtOH, to obtain corresponding desired compounds 19a-c, respectively (Tables 19 and 20).

(route ii): The 2-amino-4-benzylidenehydrazino-5-methylpyrimidine compound 18c (0.228 g, 1 mmol) and lead tetraacetate (1 mmol) were added to TFA (4 mL), and the mixture was stirred at room temperature for 15 minutes to 30 minutes. After the reaction, the solvent is removed by evaporation under reduced pressure, the residue was purified by silica gel column chromatography (Kieselgel 70-230 mesh), and the solid obtained from the AcOEt elution fraction was recrystallized from AcOEt to obtain a corresponding compound 19c (Tables 19 and 20).

Synthesis Example 18: General synthesis of 8-methyl-[1,2,4]triazolo[1,5-c]pyrimidine-5-amine compound 20a and its 2-position substituted derivative compounds 20b, c (Route iii): The 2-amino-4-hydrazino-5-methylpyrimidine 17 (0.28 g, 2 mmol) and each of triethyl orthoesters (3 mmol) were added to ethyl cellosolve (20 mL), and each mixture was heated under reflux for 0.5 hours to 32 hours. After the reaction, the solvent is removed by evaporation under reduced pressure, followed by treatment with AcOEt to precipitate crystals. The precipitated crystals were recrystallized from EtOH to obtain corresponding desired compounds 20a-c, respectively. However, for the compound 20c, it was separated and purified by silica gel column chromatography (Kieselgel 70-230 mesh), and solid components were obtained from the following fractions: AcOEt/n-hexane (n-hexane)=4/1 fraction, 2/3 fraction, and 1/3 fraction, respectively, and recrystallized from EtOH to obtain a corresponding desired compound (Tables 19 and 20). (route iv): Each of 8-methyl-[1,2,4]triazolo[4,3-c]pyrimidine-5-amine compounds 19a-c (2 mmol) was added to ethyl cellosolve (10 mL), and each mixture was heated under reflux for 12 hours. After the reaction, the solvent is removed by evaporation under reduced pressure, followed by treatment with AcOEt to precipitate crystals. The precipitated crystals were recrystallized from EtOH to obtain corresponding desired compounds 20a-c, respectively (Tables 19 and 20).

Example 6. Physical and NMR Data of the Compounds

Physical and NMR data of the compounds synthesized in Examples 1 to 5 are shown in Tables 1 to 20 below.

TABLE 1A

Physical data for compound 3a-1

| Compd. No.[a] (Formula) | Yield (%) | Mp/° C. | $v_{max}$ (Nujol)/cm$^{-1}$ | Analysis (%) Calcd. (Found) C H N | m/z MH[+b] |
|---|---|---|---|---|---|
| 3a $C_8H_{12}N_4O$ | 86 | 142-144 | 3160, 3090 (NH) 1700 (C=O) | 53.32 6.71 31.09 (53.35 6.75 31.02) | 181 |
| 3b $C_{12}H_{12}N_4O$ | 75 | 245 | 3150, 3080 (NH) 1710 (C=O) | 63.14 5.30 24.55 (63.05 5.35 24.43) | 229 |
| 3c $C_{13}H_{14}N_4O$ | 82 | 241 >224 (subli.) | 3150, 3100 (NH) 1700 (C=O) | 64.45 5.82 23.13 (64.57 5.75 23.56) | 243 |
| 3d $C_{13}H_{14}N_4O_2$ | 82 | 237-239 | 3170, 3120 (NH) 1740 (C=O) | 60.45 5.46 21.69 (60.27 5.56 21.60) | 259 |
| 3e $C_{15}H_{15}N_4O_4$ | 74 | 243-245 | 3210, 3090 (NH) 1700 (C=O) | 56.60 5.70 17.60 (56.66 5.45 17.52) | 319 |
| 3f $C_{12}H_{11}N_5O_3$ | 83 | 268-270 | 3110, 3080 (NH) 1715 (C=O) | 52.75 4.06 25.63 (52.54 4.16 25.46) | 274 |
| 3g $C_{12}H_{11}FN_4O$ | 81 | 247-249 | 3210, 3080 (NH) 1700 (C=O) | 58.53 4.50 22.75 (58.37 4.61 22.55) | 247 |
| 3h $C_{12}H_{11}FN_4O$ | 72 | 263-266 | 3210, 3100 (NH) 1700 (C=O) | 58.53 4.50 22.75 (58.28 4.81 22.44) | 247 |
| 3i $C_{12}H_{11}ClN_4O$ | 81 | 267-269 | 3220, 3100 (NH) 1700 (C=O) | 54.87 4.22 21.33 (54.87 4.41 21.08) | 263, 265 |
| 3j $C_{12}H_{10}Cl_2N_4O$ | 71 | 260-261 | 3180, 3100 (NH) 1710 (C=O) | 58.51 3.39 18.86 (48.80 3.01 18.99) | 297, 299, 301 |
| 3k $C_{12}H_{11}BrN_4O$ | 83 | 269-271 | 3210, 3090 (NH) 1700 (C=) | 46.93 3.61 18.24 (47.13 3.38 18.42) | 307, 309 |
| 3l $C_{12}H_{11}BrN_4O$ | 80 | 282-285 | 3210, 3090 (NH) 1700 (C=O) | 46.93 3.61 18.24 (47.19 3.39 18.54) | 307, 309 |

[a]All compounds were recrystallised from EtOH and obtained as colorless powder except for 3a and 3e (yellow powder).
[b]The matrix is glycerol.

TABLE 2

Table 1B Physical data for compound 3m-r

| Compd. No.[a] (Formula) | Yield (%) | Mp/° C. | $v_{max}$ (Nujol)/cm$^{-1}$ | Analysis (%) Calcd. (Found) C H N | m/z MH[+b] |
|---|---|---|---|---|---|
| 3m $C_{13}H_{11}N_5O$ | 65 | >300 | 3210, 3090 (NH) 1700 (C=O) 2230 (CN) | 61.65 4.38 27.65 (61.34 4.65 27.78) | 254 |
| 3n $C_{13}H_{12}N_4O_3$ | 70 | >300 | 3150, 3100 (NH) 1720, 1690 (C=O) | 57.35 4.44 20.58 (57.02 4.49 20.48) | 273 |
| 3o $C_{13}H_{12}N_4O_3$ | 71 | 255-257 | 3210, 3090 (NH) 1720 (C=O) | 57.35 4.44 20.58 (57.48 4.30 20.79) | 273 |
| 3p $C_{11}H_{11}N_5O$ | 69 | 274-277 | 3200, 3070 (NH) 1700 (C=O) | 57.63 4.84 30.55 (57.92 4.66 30.85) | 230 |
| 3q $C_{11}H_{11}N_5O$ | 66 | 260-262 | 3230, 3060 (NH) 1710 (C=O) | 57.63 4.84 30.55 (57.85 4.54 30.82) | 230 |
| 3r $C_{16}H_{14}N_4O$ | 65 | 252-254 | 3200, 3080 (NH) 1690 (C=O) | 69.05 5.07 20.13 (68.76 5.37 19.91) | 279 |

[a]All compounds were recrystallised from EtOH and obtained as colorless powder. [b]The matrix is glycerol.

TABLE 3

Table 2A $^1$H NMR data of compound 3a-j

| Compd. No. | $\delta_H$ [200 MHz; (CD$_3$)$_2$SO; Me$_4$Si] |
|---|---|
| 3a | 1.07 (3 H, t, J = 5.0 Hz, CHCH$_2$CH$_3$), 1.74 (3 H, d, J = 1.0 Hz, 5-Me), 2.23-2.45 (2 H, m, CHCH$_2$CH$_3$), 6.85-6.90 (1 H, m, 6-H), 7.42 (1 H, t, J = 5.0 Hz, CHCH$_2$CH$_3$), 9.25 (1 H, br s, exchangeable with D$_2$O, 4-NH), 10.09 (1 H, br s, exchangeable with D$_2$O, 1-NH) |
| 3b | 1.82 (3 H, br s, 5-Me), 6.90-7.00 (1 H, m, 6-H), 7.30-7.50 (3 H, m, Ph-m, pH), 7.90-8.10 m, Ph-oH), 8.42 (1 H, s, Ph—CH), 10.15 (1 H, br s, exchangeable with D$_2$O, 4-NH), 10.18 (1 H, br s, exchangeable with D$_2$O, 1-NH) |
| 3c | 1.81 (3 H, br s, 5-Me), 2.35 (3 H, s, Ar—Me), 6.90-6.95 (1 H, m, 6-H), 7.23 (2 H, d, J$_{AB}$ = 8.0 Hz, Ar-mH), 7.88 (2 H, d, J$_{AB}$ = 8.0 Hz, Ar-oH), 8.38 (1 H, s, Ar—CH), 10.07 (1 H, br s, exchangeable with D$_2$O, 4-NH), 10.15 (1 H, br s, exchangeable with D$_2$O, 1-NH) |
| 3d | 1.81 (3 H, br s, 5-Me), 3.81 (3 H, s, OMe), 6.90-6.93 (1 H, m, 6-H), 6.97 (2 H, d, J$_{AB}$ = 8.6 Hz, Ar-mH), 7.94 (2 H, d, J$_{AB}$ = 8.6 Hz, Ar-oH), 8.36 (1 H, s, Ar—CH), 10.05 (1 H, br s, exchangeable with D$_2$O, 4-NH), 10.12 (1 H, br s, exchangeable with D$_2$O, 1-NH) |
| 3e | 1.81 (3 H, br s, 5-Me), 3.84 (9 H, s, OMe), 6.31 (2 H, s, Ar—H), 6.87-6.91 (1 H, m, 6-H), 8.55 (1 H, s, Ar—C H), 9.09 (1 H, br s, exchangeable with D$_2$O, 4-NH), 11.17 (1 H, br s, exchangeable with D$_2$O, 1-NH) |
| 3f | 1.84 (3 H, br s, 5-Me), 7.00-7.08 (1 H, m, 6-H), 8.24 (2 H, d, J$_{AB}$ = 8.6 Hz, Ar-oH), 8.32 (2 H, d, J$_{AB}$ = 8.6 Hz, Ar-mH), 8.53 (1 H, s, Ar—CH), 10.37 (1 H, br s, exchangeable with D$_2$O, 4-NH), 10.61 (1 H, br s, exchangeable with D$_2$O, 1-NH) |
| 3g | 1.80 (3H, s, 5-Me), 6.96 (1H, s, 6-H), 7.20-7.26 (2H, m, Ar-3 and 5'-H), 7.41-7.48 (1H, m, Ar-4'-H), 8.48-8.53 (2H, m, Ar-6'-H and NH), 10.24 (1H, br s, exchangeable with D$_2$O, 4-NH), 10.28 (1H, br s, exchangeable with D$_2$O, 1-NH) |
| 3h | 1.79 (3H, s, 5-Me), 6.91 (1H, s, 6-H), 7.19-7.25 (2H, m, Ar-mH), 8.04-8.09 (2H, m, Ar-oH), 8.39 (1H, s, N═CH), 10.15 (1H, br s, exchangeable with D$_2$O, 4-NH), 10.23 (1H, br s, exchangeable with D$_2$O, 1-NH) |
| 3i | 1.79 (3H, s, 5-Me), 6.93 (1H, s, 6-H), 7.40 (2H, d, J = 8.4 Hz, Ar-mH), 8.03 (2H, d, J = 8.4 Hz, Ar-oH), 8.38 (1H, s, NH), 10.19 (1H, br s, exchangeable with D$_2$O, 4-NH), 10.30 (1H, br s, exchangeable with D$_2$O, 1-NH) |
| 3j | 1.79 (3H, s, 5-Me), 6.95 (1H, s, 6-H), 7.64 (1H, d, J$_{5',6'}$ = 8.1 Hz, Ar-5'-H), 7.90 (1H, dd, J$_{2',6'}$ = 1.5 Hz, J$_{5',6'}$ = 8.1 Hz, Ar-6'H), 8.36 (1H, s, N═CH), 8.45 (1H, d, J$_{2',6'}$ = 1.5 Hz, Ar-2'-H), 10.22 (1H, br s, exchangeable with D$_2$O, 4-NH), 10.56 (1H, br s, exchangeable with D$_2$O, 1-NH) |

TABLE 4

Table 2B $^1$H NMR data of compound 3k-r

| Compd. No. | $\delta_H$ [200 MHz; (CD$_3$)$_2$SO; Me$_4$Si] |
|---|---|
| 3k | 1.82 (3H, s, 5-Me), 6.98 (1H, s, 6-H), 7.30-7.42 (2H, m, Ar-4' and 5'-H), 7.63-7.66 (1H, m, Ar-3'-H), 8.58-8.61 (2H, m, Ar-6'-H and N═CH), 10.28 (1H, br s, exchangeable with D$_2$O, 4-NH), 10.37 (1H, br s, exchangeable with D$_2$O, 1-NH) |
| 3l | 1.79 (3H, s, 5-Me), 6.94 (1H, s, 6-H), 7.58 (2H, d, J = 8.1 Hz, Ar-mH), 7.96 (2H, d, J = 8.1 Hz, Ar-oH), 8.37 (1H, s, N═CH), 10.19 (1H, br s, exchangeable with D$_2$O, 4-NH), 10.30 (1H, br s, exchangeable with D$_2$O, 1-NH) |
| 3m | 1.82 (3 H, br s, 5-Me), 6.90-7.00 (1 H, m, 6-H), 7.30-7.50 (3 H, m, Ph-m, pH), 7.90-8.10 (2 H, m, Ph-oH), 8.42 (1 H, s, Ph—CH), 10.15 (1 H, br s, exchangeable with D$_2$O, 4-NH), 10.18 (1 H, br s, exchangeable with D$_2$O, 1-NH) |
| 3n | 1.81 (3 H, br s, 5-Me), 2.35 (3 H, s, Ar—Me), 6.90-6.95 (1 H, m, 6-H), 7.23 (2 H, d, J$_{AB}$ = 8.0 Hz, Ar-mH), 7.88 (2 H, d, J$_{AB}$ = 8.0 Hz, Ar-oH), 8.38 (1 H, s, Ar—CH), 10.07 (1 H, br s,exchangeable with D$_2$O, 4-NH), 10.15 (1 H, br s, exchangeable with D$_2$O, 1-NH) |
| 3o | 1.81 (3 H, br s, 5-Me), 3.81 (3 H, s, OMe), 6.90-6.93 (1 H, m, 6-H), 6.97 (2 H, d, J$_{AB}$ = 8.6 Hz, Ar-mH), 7.94 (2 H, d, JAB = 8.6 Hz, Ar-oH), 8.36 (1 H, s, Ar—CH), 10.05 (1 H, br s, exchangeable with D$_2$O, 4-NH), 10.12 (1 H, br s, exchangeable with D$_2$O, 1-NH) |
| 3p | 1.81 (3 H, br s, 5-Me), 3.84 (9 H, s, OMe), 6.31 (2 H, s, Ar—H), 6.87-6.91 (1 H, m, 6-H) 8.55 (1 H, s, Ar—C H), 9.09 (1 H, br s, exchangeable with D$_2$O, 4-NH), 11.17 (1 H, br s, exchangeable with D$_2$O, 1-NH) |
| 3q | 1.84 (3 H, br s, 5-Me), 7.00-7.08 (1 H, m, 6-H), 8.24 (2 H, d, J$_{AB}$ = 8.6 Hz, Ar-oH), 8.32 (2 H, d, J$_{AB}$ = 8.6 Hz, Ar-mH), 8.53 (1 H, s, Ar—CH), 10.37 (1 H, br s, exchangeable with D$_2$O, 4-NH), 10.61 (1 H, br s, exchangeable with D$_2$O, 1-NH) |
| 3r | 1.80 (3H, s, 5-Me), 6.96 (1H, s, 6-H), 7.20-7.26 (2H, m, Ar-3' and 5'-H), 7.41-7.48 (1H, m, Ar-4'-H), 8.48-8.53 (2H, m, Ar-6'-H and N═CH), 10.24 (1H, br s, exchangeable with D$_2$O, 4-NH), 10.28 (1H, br s, exchangeable with D$_2$O, 1-NH) |

TABLE 5

Table 3 Physical data for compound 4a-f and 4s, t

| Compd.No.[a] (Formula) | Yield (%) (route)[b] | Mp/° C. | $v_{max}$ (Nujol)/cm$^{-1}$ | $\lambda_{max}$/nm (log ε dm$^3$ mol$^{-1}$ cm$^{-1}$)[d] | m/z: MH[+f] |
|---|---|---|---|---|---|
| 4a C$_8$H$_{10}$N$_4$O | 91 (i) | 272-273[c] >190 (subli.) | 3070 (NH) 1740 (C=O) | 262 (3.95) | 179 |
| 4b C$_{12}$H$_{10}$N$_4$O | 65 (i) 64 (ii) | 274-276[c] >190 (subli.) | 3070 (NH) 1740 (C=O) | [e] | 227 |
| 4c C$_{13}$H$_{12}$N$_4$O | 78 (i) | 285 >211 (subli.) | 3060 (NH) 1750 (C=O) | [e] | 241 |
| 4d C$_{13}$H$_{12}$N$_4$O$_2$ | 91 (ii) | 277-278 | 3060 (NH) 1740 (C=O) | [e] | 257 |
| 4e C$_{15}$H$_{16}$N$_4$O$_4$ | 55 (ii) | 178 | 3090 (NH) 1740 (C=O) | [e] | 317 |
| 4f C$_{12}$H$_9$N$_5$O$_3$ | 58 (i) | >300[c] | 3070 (NH) 1750 (C=O) | [e] | 272 |
| 4s C$_{13}$H$_{11}$N$_5$O$_4$ | 56 (i) | >298 (decamp.) | 3070 (NH) 1750 (C=O) | 256 (3.90) | 302 |
| 4t C$_{15}$H$_{15}$N$_5$O$_6$ | 53 (i) | 178-180 | 3090 (NH) 1740 (C=O) | 263 (3.84) | 362 |

[a]Because all compound [4,3-c]isomers were isomerised into their [1,5-c] isomers in solvent, the elemental analyses were impossible. [b]Route i: HNO$_3$, TFA, nt.-40° C.; route ii: Pb(OAc)$_4$, TFA, r.t., [c]This compound [4,3-c] isomer was isomerised into it's [1,5-c] isomer at the temperature under melting point. [d]All UV spectra were measured in EtOH. [e]Because this compound was isomerised immediately, the accurate UV spectrum was not obtained. [f]The matrix is glycerol.

TABLE 6

Table 4 $^1$H NMR data of compound 4a-f and 4s, t

| Compd. No. | δ$_H$ [200 MHz; (CD$_3$)$_2$SO; Me$_4$Si] |
|---|---|
| 4a | 1.29 (3 H, t, J = 7.4 Hz, CH$_2$CH$_3$), 2.14 (3 H, d, J = 1.4 Hz, 8-Me), 3.17 (3 H, q, J = 7.4 Hz, CH$_2$CH$_3$), 6.97-7.00 (1 H, m, 7-H), 11.32 (1H, br s, exchangeable with D$_2$O, NH) |
| 4b | 2.23 (3 H, d, J = 1.2 Hz, 8-Me), 7.10-7.14 (1 H, m, 7-H), 7.40-7.60 (3 H, m, Ph-m, pH), 7.70-7.80 (2 H, m, Ph-oH), 11.42 (1 H, br s, exchangeable with D$_2$O, NH) |
| 4c | 2.22 (3 H, d, J = 1.2 Hz, 8-Me), 2.39 (3 H, s, Ar—Me), 7.08-7.12 (1 H, m, 7-H), 7.28 (2 H, d, J$_{AB}$ = 8.0 Hz, Ar-mH), 7.62 (2 H, d, J$_{AB}$ = 8.0 Hz, Ar-oH), 11.39 (1 H, br s, exchangeable with D$_2$O, NH) |
| 4d | 2.22 (3 H, br s, 8-Me), 3.84 (3 H, s, OMe), 7.03 (2 H, d, J$_{AB}$ = 8.8 Hz, Ar-mH), 7.06-7.11 (1 H, m, 7-H), 7.69 (2 H, d, J$_{AB}$ = 8.8 Hz, Ar-oH), 11.38 (1 H, br s, exchangeable with D$_2$O, NH) |
| 4e | 2.20 (3 H, br s, 8-Me), 3.65 (6 H, s, 2'-OMe and 6'-OMe), 3.86 (3 H, s, 4'-OMe), 6.31 (2 H, s, 3'-H and 5'-H), 7.00-7.10 (1 H, m, 7-H), 11.26 (1 H, br s, exchangeable with D$_2$O, NH) |
| 4f | 2.26 (3 H, br s, 8-Me), 7.15-7.25 (1 H, s, 7-H), 8.05 (2 H, d, J$_{AB}$ = 8.6 Hz, Ar-mH), 8.34 (2 H, d, J$_{AB}$ = 8.6 Hz, Ar-oH), 11.62 (1 H, br s, exchangeable wtih D$_2$O, NH) |
| 8s | 2.23 (3 H, br s, 8-Me), 4.01 (3 H, s, OMe), 7.10-7.20 (1 H, m, 7-H), 7.49 (1 H, d, J$_{5',6'}$ = 8.8 Hz, 5'-H), 8.06 (1H, dd, J$_{5',6'}$ = 8.8 Hz, J$_{2',6'}$ = 2.2 Hz, 6'-H), 8.30 (1H, d, J$_{2',6'}$ = 2.2 Hz, 2'-H), 11.48 (1H, br s, exchangeable with D$_2$O, NH) |
| 8t | 2.23 (3 H, br s, 8-Me), 3.50 (3 H, s, 6'-OMe), 3.89 (3 H, s, 2'-OMe), 4.01 (3 H, s, 4'-OMe), 6.77 (1 H, s, Ar—H), 7.10-7.15(1 H, m, 7-H), 11.49 (1 H, br s, exchangeable with D$_2$O, NH) |

TABLE 7

Table 5A Physical data for compound 5a-k

| Compd, No.[a] (Formula) | Yield (%) (route)[b] | Mp/° C. | $v_{max}$ (Nujol)/cm$^{-1}$ | $\lambda_{max}$/nm (log ε/dm$^3$ mol$^{-1}$ cm$^{-1}$)[c] | Analysis (%) Calcd. (Found) C / H / N | | | m/z MH[+d] |
|---|---|---|---|---|---|---|---|---|
| 5a C$_8$H$_{10}$N$_4$O | 71 (iii) | 273-274 >193 (subli.) | 3070 (NH) 1740 (C=O) | 244 (3.79), 252 (3.82), 270 (3.88) | 53.92 (53.94) | 5.66 (5.51) | 31.44 (31.40) | 179 |
| 5b C$_{12}$H$_{10}$N$_4$O | 71 (iii) | 274-275 | 3060 (NH) 1720 (C=O) | 246 (4,42), 280 (3.82) | 63.71 (63.87) | 4.46 (4.64) | 24.77 (24.75) | 227 |
| 5c C$_{13}$H$_{12}$N$_4$O | 81 (iii) | 293-294 | 3090 (NH) 1720 (C=O) | 252 (4.41), 283 (3.78) | 64.99 (65.00) | 5.03 (5.13) | 23.32 (23.21) | 241 |
| 5d C$_{13}$H$_{12}$N$_4$O$_2$ | 86 (iii) | 288-289 | 3060 (NH) 1750(C=O) | 264 (4.46) | 60.93 (61.01) | 4.72 (4.86) | 21.86 (21.87) | 257 |
| 5e C$_{15}$H$_{16}$N$_4$O$_4$ | 75 (iii) | 285-287 >275 (subli.) | 3070 (NH) 1720 (C=O) | 206 (4.74), 252 (4.14), 278 (4.00) | 56.96 (56.71) | 5.10 (5.25) | 17.71 (17.63) | 317 |
| 5f C$_{12}$H$_9$N$_5$O$_3$ | 77 (iii) | 300 | 3090 (NH) 1740 (C=O) | 218 (420), 282 (4.35) | 53.14 (52.97) | 3.34 (3.63) | 25.82 (25.70) | 272 |
| 5g C$_{12}$H$_9$FN$_4$O | 65 (iii) | 264-268 | 3090 (NH) 1740 (C=O) | 245 (4.31), 268 (4.01) | 59.02 (58.92) | 3.71 (3.89) | 22.94 (22.88) | 245 |
| 5h C$_{12}$H$_9$FN$_4$O | 64 (iii) | 300 | 3090 (NH) 1720 (C=O) | 250 (4.47) | 59.02 (58.28) | 3.71 (3.99) | 22.94 (22.75) | 245 |
| 5i | 53 (iii) | 278-280 | 3070 (NH) | 253 (4.52) | 55.29 | 3.48 | 21.49 | 261, |

TABLE 7-continued

Table 5A Physical data for compound 5a-k

| Compd. No.[a] (Formula) | Yield (%) (route)[b] | Mp/° C. | $\nu_{max}$ (Nujol)/cm$^{-1}$ | $\lambda_{max}$/nm (log ε/dm$^3$ mol$^{-1}$ cm$^{-1}$)[c] | Analysis (%) Calcd. (Found) C H N | | | m/z MH$^{+d}$ |
|---|---|---|---|---|---|---|---|---|
| C$_{12}$H$_9$ClN$_4$O | | | 1720 (C=O) | | (55.38 | 3.57 | 21.19) | 263 |
| 5j C$_{12}$H$_8$Cl$_2$N$_4$O | 68 (iii) | 300 | 3160 (NH) 1770 (C=O) | 254 (4.53) | 48.84 (48.99 | 2.73 2.96 | 18.98 18.71) | 295, 297, 299 |
| 5k C$_{12}$H$_9$BrN$_4$O | 67 (iii) | 226-228 | 3070 (NH) 1760 (C=O) | 244 (4.15) | 47.24 (47.56 | 2.97 2.68 | 18.36 18.15) | 305, 307 |

[a]All compounds were recrystallised from EtOH and obtained as colorless needles except for 5e (pale yellow powder). [b]Route iii: 70% HNO$_3$, DMF, 100° C.-reflux. [c]All UV spectra were measured in EtOH. The italic values refer to wave lengths at which shoulders or inflections occur in the absorption. [d]The matrix is glycerol.

TABLE 8

Table 5B Physical data for compound 514

| Compd. No.[a] (Formula) | Yield (%) (route)[b] | Mp/° C. | $\nu_{max}$ (Nujol)/cm$^{-1}$ | $\lambda_{max}$/nm (log ε/dm$^3$ mol$^{-1}$ cm$^{-1}$)[c] | Analysis (%) Calcd. (Found) C H N | | | m/z MH$^{+d}$ |
|---|---|---|---|---|---|---|---|---|
| 5l C$_{12}$H$_9$BrN$_4$O | 65 (iii) | 261-263 | 3700 (NH) 1730 (C=O) | 256 (4.50) | 47.24 (47.03 | 2.97 2.95 | 18.36 18.55) | 305, 307 |
| 5m C$_{13}$H$_9$N$_5$O | 62 (iii) | >300 | 3120 (NH) 1740 (C=O) 2230 (CN) | 264 (4.52) | 62.15 (62.32 | 3.61 3.38 | 27.87 27.91) | 252 |
| 5n C$_{13}$H$_{10}$N$_4$O$_3$ | 58 (iii) | >300 | 3100 (NH) 1720, 1700 (C=O) | 260 (4.44) | 57.78 (57.52 | 3.73 3.96 | 20.73 20.49) | 271 |
| 5o C$_{13}$H$_{10}$N$_4$O$_3$ | 70 (iii) | >300 | 3080 (NH) 1720 (C=) | 264 (4.24) | 57.78 (57.93 | 3.73 3.48 | 20.73 20.79) | 271 |
| 5p C$_{11}$H$_9$N$_5$O | 55 (iii) | >300 | 3060 (NH) 1760 (C=O) | 266 (4.49) | 58.14 (58.33 | 3.99 3.77 | 30.82 30.99) | 228 |
| 5q C$_{11}$H$_9$N$_5$O | 64 (iii) | >300 | 3030 (NH) 1720 (C=O) | 245 (4.36), 264 (4.21) | 58.14 (58.32 | 3.99 4.09 | 30.82 30.49) | 228 |
| 5r C$_{16}$H$_{12}$N$_4$O | 57 (iii) | 284-285 | 3080 (NH) 1740 (C=O) | 261 (4.11) | 69.55 (69.21 | 4.38 4.56 | 20.28 20.10) | 277 |
| 5s C$_{13}$H$_{11}$N$_5$O$_4$•1/2H$_2$O | 90 (iv) | 299-301 | 3060 (NH) 1740 (C=O) | 256 (4.25) | 50.32 (50.32 | 3.90 4.09 | 22.57 22.58) | 302 |
| 5t C$_{15}$H$_{15}$N$_5$O$_6$•1/2H$_2$O | 80 (iv) | 167-169 | 3070 (NH) 1730 (C=O) | 247 (4.07), 275 (3.96) | 48.65 (48.68 | 4.35 4.15 | 18.91 19.01) | 362 |

[a]All compounds were recrystallised from EtOH and obtained as colorless needles. [b]Route iii: 70% HNO$_3$, DMF. 100° C.-reflux, route iv: EtOH or DMSO r.t.-100° C. [c]All UV spectra were measured in EtOH. The italic values refer to wave lengths at which shoulders or inflections occur in the absorption. [d]The matrix is glycerol.

TABLE 9

Table 6A $^1$H NMR data of compounds 5a-k

| Compd. No. | $\delta_H$ [200 MHz; (CD$_3$)$_2$SO; Me$_4$Si] |
|---|---|
| 5a | 1.28 (3 H, t, J = 7.4 Hz, CH$_2$CH$_3$), 2.17 (3 H, d, J = 1.4 Hz, 8-Me), 2.78 (3 H, q, J = 7.4 Hz CH$_2$CH$_3$), 7.30-7.40 (1 H, m, 7-H), 11.76 (1H, br s, exchangeable with D$_2$O, NH), |
| 5b | 2.26 (3 H, d, J = 1.4 Hz, 8-Me), 7.40-7.45 (1 H, m, 7-H), 7.35-7.70 (3 H, m, Ph-m, pH), 8.10-8.35 (2 H, m, Ph-oH), 11.90 (1 H, br s, exchangeable with D$_2$O, NH) |
| 5c | 2.25 (3 H, d, J = 1.2 Hz, 8-Me), 2.39 (3 H, s, Ar—Me), 7.35 (2 H, d, J$_{AB}$ = 8.0 Hz, Ar-mH), 7.40-7.45 (1 H, m, 7-H), 8.07 (2 H, d, J$_{AB}$ = 8.0 Hz, Ar-oH), 11.89 (1 H, br s, exchangeable with D$_2$O, NH) |
| 5d | 2.24 (3 H, br s, 8-Me), 3.84 (3 H, s, OMe), 7.09 (2 H, d, J$_{AB}$ = 9.0 Hz, Ar-mH), 7.37-7.43 (1 H, m, 7-H), 8.11 (2 H, d, J$_{AB}$ = 9.0 Hz, Ar-oH), 11.85 (1 H, br, exchangeable with D$_2$O, NH) |
| 5e | 2.19 (3 H, br s, 8-Me), 3.67 (6 H, s, 2' and 6'-OMe), 3.85 (3 H, s, 4'-OMe), 6.33 (2 H, s, Ar-mH), 7.30-7.40 (1 H, m, 7-H), 11.84 (1 H, br s, exchangeable with D$_2$O, NH) |
| 5f | 2.27 (3 H, br s, 8-Me), 7.44-7.50 (1 H, m, 7-H), 8.30-8.55 (4 H, m, Ar—H), 12.01 (1 H, br s, exchangeable with D$_2$O, NH) |
| 5g | 2.22 (3H, s, 8-Me), 7.33-7.42 (2H, m, Ar-3' and 5'-H), 7.42 (1H, s, 7-H), 7.55-7.57 (1H, m, Ar-4'-H), 8.01-8.15 (1H, m, Ar-6'-H), 11.90 (1H, br s, exchangeable with D$_2$O, NH) |
| 5h | 2.25 (3H, s, 8-Me), 7.38 (2H, dd, J$_{H,F}$ = 9.0 Hz, J$_{oH,mH}$ = 8.7 Hz, Ar-mH), 7.43 (1 H, s, 7-H), 8.22 (2H, dd, J$_{H,F}$ = 5.7 Hz, J$_{oH,mH}$ = 8.7 Hz, Ar-oH), 11.92 (1H, br s, exchangeable with D$_2$O, NH) |
| 5i | 2.25 (3H, s, 8-Me), 7.44 (1H, s, 7-H), 7.60 (2H, d, J = 8.4 Hz, Ar-mH), 8.18 (2H, d, J = 8.4 Hz, Ar-oH), 11.94 (1H, br s, exchangeable with D$_2$O, NH) |

TABLE 9-continued

Table 6A ¹H NMR data of compounds 5a-k

| Compd. No. | $\delta_H$ [200 MHz; (CD$_3$)$_2$SO; Me$_4$Si] |
|---|---|
| 5j | 2.25 (3H, d, J = 0.9 Hz, 8-Me), 7.44 (1H, s, 7-H), 7.80 (1H, d, J$_{5',6'}$ = 8.4 Hz, Ar-5'-H), 8.12 (1H, dd, J$_{5',6'}$ = 8.4 Hz, J$_{2',6'}$ = 1.8 Hz, Ar-6'-H), 8.27 (1H, d, J$_{2',6'}$ = 1.8 Hz, Ar-2'-H), 11.94 (1H, br s, exchangeable with D$_2$O, NH) |
| 5k | 2.22 (3H, d, J = 1.2 Hz, 8-Me), 7.42 (1H, s, 7-H), 7.42-7.52 (2H, m, Ar-4' and 5'-H), 7.55-7.83 (2H, m, Ar-3' and 6'-H), 11.96 (1H, br s, exchangeable with D$_2$O, NH) |

TABLE 10

Table 6B ¹H NMR data of compounds 5l-t

| Compd. No. | $\delta_H$ [200 MHz; (CD$_3$)$_2$SO; Me$_4$Si] |
|---|---|
| 5l | 2.25 (3H, s, 8-Me), 7.43 (1H, s, 7-H), 7.75 (2H, d, J = 8.4 Hz, Ar-mH), 8.11 (2H, d, J = 8.4Hz, Ar-oH), 11.93 (1H, br s, exchangeable with D$_2$O, NH) |
| 5m | 2.20 (3H, s, 8-Me), 7.43 (1H, s, 7-H), 7.98 (2H, d, J = 8.4 Hz, Ar-mH), 8.29 (2H, d, J = 8.4 Hz, Ar-oH), 11.97 (1H, br s, exchangeable with D$_2$O, NH) |
| 5n | 2.27 (3H, s, 8-Me), 7.42 (1H, s, 7-H), 8.09 (2H, d, J = 8.4 Hz, Ar-oH), 8.29 (2H, d, J = 8.4 Hz, Ar-mH), 11.94 (1H, br s, exchangeable with D$_2$O, NH), 13.10 (1H, br s, exchangeable with D$_2$O, COOH) |
| 5o | 2.22 (3H, d, J = 1.2 Hz, 8-Me), 6.12 (2H, s, —O—CH$_2$—O—), 7.05 (1H, d, J$_{5',6'}$ = 8.1 Hz, Ar-5'-H), 7.37-7.40 (1H, br s, 7-H), 7.59 (1H, d, J$_{2',6'}$ = 1.5 Hz, Ar-2'-H), 7.74 (1H, d, J$_{2',6'}$ = 1.5 Hz, J$_{5',6'}$ = 8.1 Hz, Ar-6'-H), 11.85 (1H, br s, exchangeable with D$_2$O, NH) |
| 5p | 2.23 (3H, s, 8-Me), 7.43 (1H, s, 7-H), 7.56 (1H, dd, J$_{4',5'}$ = 8.1 Hz, J$_{5',6'}$ = 4.5 Hz, Ar-5'-H), 8.45 (1H, dd, J$_{2',4'}$ = 1.8 Hz, J$_{4',5'}$ = 8.1 Hz, Ar-4'-H), 8.70 (1H, d, J$_{5',6'}$ = 4.5 Hz, Ar-6'-H), 9.29 (1H, s, J$_{2',4'}$ = 1.8 Hz, Ar-2'-H), 11.94 (1H, br s, exchangeable with D$_2$O, NH) |
| 5q | 2.23 (3H, s, 8-Me), 7.44 (1H, s, 7-H), 8.05 (2H, d, J = 4.8 Hz, Ar-3' and 5'-H), 8.74 (2H, d, J = 4.8 Hz, Ar-2' and 6'-H), 11.99 (1H, br s, exchangeable with D$_2$O, NH) |
| 5r | 2.30 (3H, d, J = 1.2 Hz, 8-Me), 7.42 (1H, s, 7-H), 7.57-7.61 (2H, m, Ar-6' and 7'-H), 7.96-8.14 (3H, m, Ar-4', 5' and 8'-H), 8.37 (1H, dd, J$_{3',4'}$ = 8.4 Hz, J$_{1',3'}$ = 1.8 Hz, Ar-3'-H), 8.77 (1H, d, J$_{1',3'}$ = 1.8 Hz, Ar-1'-H), 11.91 (1H br s exchangeable with D$_2$O, NH) |
| 5s | 2.25 (3 H, br s, 8-Me), 4.01 (3 H, s, OMe), 7.40-7.50 (1 H, m, 7-H), 7.55 (1 H, d, J$_{5',6'}$ = 8.8 Hz, 5'-H), 8.41 (1 H, dd, J$_{5',6'}$ = 8.8 Hz, J$_{2',6'}$ = 2.0 Hz 6'-H), 8.56 (1 H, d, J$_{2',6'}$ = 2.0 Hz, 2'-H), 11.96 (1 H, br s, exchangeable with D$_2$O, NH) |
| 5t | 2.21 (3 H, br s, 8-Me), 3.54 (3 H, s, 2'-OMe), 3.83 (3 H, s, 6'-OMe), 4.01 (3 H, s, 4'-OMe), 6.79 (1 H, s, Ar—H), 7.40-7.50 (1 H, m, 7-H), 11.98 (1 H, br s, exchangeable with D$_2$O, NH) |

TABLE 11

Table 7 Physical data for compound 6b, f, j, l, m

| Compd. No.[a] (Formula) | Yield (%) | Mp/° C. | $\nu_{max}$ (Nujol)/cm$^{-1}$ | Analysis (%) Calcd. (Found) C | H | N | m/z: MH$^{+b}$ |
|---|---|---|---|---|---|---|---|
| 6b C$_{12}$H$_9$ClN$_4$ | 42 | 151-155 | 249 (4.53) | 58.91 (58.69) | 3.71 (3.91) | 22.90 (22.99) | 245, 247 |
| 6l C$_{12}$H$_8$ClN$_5$O$_2$ | 51 | 166-168 | 285 (4.33) | 49.76 (49.60) | 2.78 (2.99) | 24.18 (24.48) | 290, 292 |
| 6j C$_{12}$H$_7$Cl$_3$N$_4$ | 32 | 162-165 | 254 (4.48) | 45.97 (45.77) | 2.25 (2.50) | 17.87 (17.99) | 313, 315, 317 |
| 6l C$_{12}$H$_8$BrClN$_4$ | 43 | 165-168 | 255 (4.60) | 44.54 (44.83) | 2.49 (2.66) | 17.32 (17.07) | 323, 325, 327 |
| 6m C$_{13}$H$_8$ClN$_5$ | 27 | 245-248 | 256 (4.59) | 57.90 (58.08) | 2.99 (2.71) | 25.97 (25.72) | 270, 272 |

[a]All compounds were recrystallised from EtOH and obtained as colorless needles or powder. [b]All UV spectra were measured in EtOH. [c]The matrix is glycerol.

TABLE 12

Table 8 ¹H NMR data of compounds 6b, f, j, l, m

| Compd. No. | $\delta_H$ [300 MHz; (CD$_3$)$_2$SO; Me$_4$Si] |
|---|---|
| 6b | 2.63 (3H, s, 8-Me), 7.48-7.53 (3H, m, Ph-m, pH), 7.91 (1H, s, 7-H), 8.34-8.37 (2H, m, Ph-oH) |
| 6f | 168 (3H, s, 8-Me), 7.99 (1H, s, 7-H), 8.39-8.55 (4H, m, Ar-o, mH) |

TABLE 12-continued

Table 8 $^1$H NMR data of compounds 6b, f, j, l, m

| Compd. No. | $\delta_H$ [300 MHz; (CD$_3$)$_2$SO; Me$_4$Si] |
|---|---|
| 6j | 2.62 (3H, s, 8-Me), 7.59 (1H, d, J$_{5',6'}$ = 7.8 Hz, Ar-5'-H), 7.94 (1H, s, 7-H), 8.19 (1H, dd J$_{2',6'}$ = 7.8 Hz, Ar-6'-H), 8.46 (1H, d, J$_{2',6'}$ = 1.8 Hz, Ar-2'-H) |
| 6l | 2.62 (3H, s, 8-Me), 7.65 (2H, d, J = 8.4 Hz, Ar-mH), 7.92 (1H, s, 7-H), 8.24 (2H, d, J = 8.4 Hz, Ar-oH) |
| 6m | 2.64 (3H, s, 8-Me), 7.82 (2H, d, J = Ar-mH), 7.96 (1H, s, 7-H), 8.49 (2H, J = 8.4 Hz, Ar-oH) |

TABLE 13

Table 9 Physical data for compound 8d-g

| Compd. No.$^a$ (Formula) | Yield (%) | Mp/° C. | $\nu_{max}$ (Nujol)/cm$^{-1}$ | Analysis (%) Calcd. (Found) C H N | m/z: MH$^{+b}$ |
|---|---|---|---|---|---|
| 8d C$_{11}$H$_9$FN$_4$O | 72 | 245-247 | 3200, 3090 (NH), 1700 (C=O) | 56.90 3.91 24.13 (56.72 4.06 24.00) | 233 |
| 8e C$_{11}$H$_7$Cl$_2$FN$_4$O | 75 | 275-279 | 3180, 3100 (NH), 1710 (C=O) | 43.88 2.34 18.61 (44.12 2.11 18.52) | 301, 303, 305 |
| 8f C$_{11}$H$_8$BrFN$_4$O | 64 | 264-266 | 3220, 3090 (NH), 1710 (C=O) | 42.47 239 18.01 (42.63 2.74 17.79) | 311, 313 |
| 8g C$_{12}$H$_8$FN$_5$O | 73 | 298-300 | 3180, 3100 (NH), 1720 (C=O), 2230 (CN) | 56.03 3.13 27.23 (56.28 3.25 27.02) | 258 |

$^a$All compounds were recrystallised from EtOH and obtained as colorless needles or powder. $^b$The matrix is glycerol.

TABLE 14

Table 10 $^1$H NMR data of compounds 8d-g

| Compd. No. | $\delta_H$ [300 MHz; (CD$_3$)$_2$SO; Me$_4$Si] |
|---|---|
| 8d | 7.38 (1H, d, J$_{F,H}$ = 6.3 Hz, 6-H), 7.39-7.56 (3H, m, Ph-m, pH), 8.02-8.03 (2H, m, Ph-oH), 8.40 (1H, s, N=CH), 10.22 (1H, br s, exchangeable with D$_2$O, 4-NH), 10.65 (1H, br s, exchangeable with D$_2$O, 1-NH) |
| 8e | 7.43 (1H, d, J$_{F,H}$ = 6.3Hz, 6-H), 7.67 (1H, d, J = 8.1 Hz, Ar-5'-H), 7.92 (1H, d, J = 8.1 Hz, Ar-6'-H), 8.38 (1H, s, N=CH), 8.49 (1H, s, Ar-1'-H), 10.24 (1H, br s, exchangeable with D$_2$O, 4-NH), 11.00 (1H, br s, exchangeable with D$_2$O, 1-NH) |
| 8f | 7.38 (1H, d, J$_{F,H}$ = 6.9 Hz, 6-H), 7.60 (2H, d, J = 8.4 Hz, Ar-mH), 8.00 (2H, d, J = 8.4 Hz, Ar-oH), 8.38 (1H, s, N=CH), 10.20 (1H, br s, exchangeable with D$_2$O, 4-NH), 10.82 (1H, br s, exchangeable with D$_2$O, 1-NH) |
| 8g | 7.46 (1H, d, J$_{F,H}$ = 6.0 Hz, 6-H), 7.87 (2H, d, J = 7.8 Hz, Ar-mH), 8.24 (2H, d, J = 7.8 Hz, Ar-oH), 8.46 (1H, s, N=CH), 10.31 (1H, br s, exchangeable with D$_2$O, 4-NH), 11.02 (1H, br s, 1-NH) |

TABLE 15

Table 11 Physical data for compound 9a-g

| Compd. No.$^a$ (Formula) | Yield (%) | Mp/° C. | $\nu_{max}$ (Nujol)/cm$^{-1}$ | $\lambda_{max}$/nm (log ε/dm$^3$ mol$^{-1}$ cm$^{-1}$)$^b$ | Analysis (%) Calcd. (Found) C H N | m/z MH$^{+c}$ |
|---|---|---|---|---|---|---|
| 9a C$_5$H$_3$FN$_4$O | 81 | 195-198 | 3090 (NH) 1700 (C=O) | 253 (3.74), 270 (3.82) | 38.97 1.96 36.36 (38.76 1.91 36.53) | 155 |
| 9b C$_6$H$_5$FN$_4$O | 72 | 250-252 | 3110 (NH) 1760 (C=O) | 272 (3.89) | 42.86 3.00 33.32 (42.97 3.27 33.01) | 169 |
| 9c C$_7$H$_7$FN$_4$O | 72 | 260-262 | 3110 (NH) 1750 (C=O) | 272 (3.85) | 46.16 3.87 30.76 (46.41 3.99 30.49) | 183 |
| 9d C$_1$H$_7$FN$_4$O | 65 | >300 | 3060 (NH) 1750 (C=O) | 247 (4.39) | 57.39 3.07 24.34 (57.13 3.38 24.54) | 231 |
| 9e C$_{11}$H$_5$Cl$_2$FN$_4$O | 66 | >300 | 3090 (NH) 1750 (C=O) | 254 (4.52) | 44.17 1.69 18.73 (44.09 1.88 18.51) | 299 301 303 |
| 9f | 60 | >300 | 3070 (NH) | 256 (4.56) | 42.74 1.96 18.13 | 309 |

TABLE 15-continued

Table 11 Physical data for compound 9a-g

| Compd. No.[a] (Formula) | Yield (%) | Mp/° C. | $v_{max}$ (Nujol)/cm$^{-1}$ | $\lambda_{max}$/nm (log ε/dm$^3$ mol$^{-1}$ cm$^{-1}$)[b] | Analysis (%) Calcd. (Found) | | | m/z MH$^{+c}$ |
|---|---|---|---|---|---|---|---|---|
| | | | | | C | H | N | |
| $C_{11}H_6BrFN_4O$ | | | 1720 (C=O) | | (42.97 | 1.89 | 18.03) | 311 |
| 9g | 58 | >300 | 3100 (NH) | 259 (4.60) | 56.48 | 2.37 | 27.44 | 256 |
| $C_{12}H_6FN_5O$ | | | 1750 (C=O) | | (56.69 | 2.57 | 27.28) | |
| | | | 2240 (CN) | | | | | |

[a]All compounds were recrystallised from EtOH and obtained as colorless needles or powder. [b]All UV spectra were measured in EtOH. [c]The matrix is glycerol.

TABLE 16

Table 12 $^1$H NMR data of compounds 9a-g

| Compd. No. | $\delta_H$ [200 MHz; (CD$_3$)$_2$SO; Me$_4$Si] |
|---|---|
| 9a | 7.93 (1H, d, $J_{F,H}$ = 5.1 Hz, 7-H), 8.49 (1H, s, 2-H), 12.05 (1H, br s, exchangeable with D$_2$O, NH) |
| 9b | 2.42 (3H, s, 2-Me), 7.88 (1H, d, $J_{F,H}$ = 5.4 Hz, 7-H), 11.85 (1H, br s, exchangeable with D$_2$O, NH) |
| 9c | 1.27 (3H, t, J = 7.5 Hz, 2-CH$_2$CH$_3$), 2.79 (2H, q, J = 7.5 Hz, 2-CH$_2$CH$_3$), 7.88 (1H, d, $J_{F,H}$ = 5.4 Hz, 7-H), 11.91 (1H, br s, exchangeable with D$_2$O, NH) |
| 9d | 7.53-7.60 (3H, m, Ph-m, pH), 7.97 (1H, d, $J_{F,H}$ = 5.4 Hz, 7-H), 8.13-8.18 2H, m, Ph-oH), 12.05 (1H, br s, exchangeable with D$_2$O, NH) |
| 9e | 7.81 (1H, d, $J_{5',6'}$ = 8.4 Hz, Ar-5'-H), 8.00 (1H, d, $J_{F,H}$ = 5.1 Hz, 7-H), 8.10 (1H, dd, $J_{5',6'}$ = 8.4 Hz, $J_{2',6'}$ = 1.8 Hz, Ar-6'-H), 8.26 (1H, d, $J_{5',6'}$ = 1.8 Hz, Ar-2'-H), 12.13 (1H, br s, exchangeable with D$_2$O, NH) |
| 9f | 7.74 (2H, d, J = 8.4 Hz, Ar-mH), 7.97 (1H, d, $J_{F,H}$ = 5.1 Hz, 7-H), 8.09 (2H, d, J = 8.4 Hz, Ar-oH), 12.08 (1H, br s, exchangeable with D$_2$O, NH) |
| 9g | 8.00-8.02 (3H, m, Ar-mH, 7-H), 8.28 (2H, d, J = 7.2 Hz, Ar-oH), 12.16 (1H, br s, exchangeable with D$_2$O, NH) |

TABLE 17

Table 13 Physical data for compounds 12b, c,13a, b and 14a-c.

| Compd. No.[a] (Formula) | Yield (%) (route)[b] | Mp/° C. | $v_{max}$ (Nujol)/cm$^{-1}$ | $\lambda_{max}$/nm (log ε/dm$^3$ mol$^{-1}$ cm$^{-1}$)[d] | Analysis (%) Calcd. (Found) | | | m/z MH$^{+f}$ |
|---|---|---|---|---|---|---|---|---|
| | | | | | C | H | N | |
| 12b $C_7H_{10}N_4S\cdot1/10H_2O$ | 82 | 215 | 3190, 3120 (NH) | | 45.68 (45.87) | 5.59 5.57 | 30.44 30.14) | 183 |
| 12c $C_{12}H_{12}N_4S\cdot1/2H_2O$ | 77 | 248 | 3150, 3100 (NH) | | 56.89 (58.77 | 5.17 5.32 | 22.12 22.20) | 245 |
| 13a $C_6H_6N_4S$ | 89 (i) | >291 (decomp.)[c] >242 (subli.) | 3070 (NH) | 252 (3.45), 313 (4.17), 321 (4.21), 334 (4.05) | [e] | | | 167 |
| 13b $C_7H_8N_4S$ | 49 (ii) | >258 (decomp.) | 3070 (NH) | 250 (3.53), 323 (4.04) | [e] | | | 181 |
| 14a $C_6H_6N_4S$ | 69 (iii) | >300 >243 (subli.) | 3070 (NH) | 236 (3.72), 306 (4.30) 340 (3.47) | 43.36 (43.25 | 3.64 3.76 | 33.71 33.63) | 167 |
| 14b $C_7H_8N_4S$ | 64 (iii) | 294-296 (decomp.) | 3075 (NH) | 239 (3.85), 304 (4.33) | 46.65 (46.42 | 4.47 4.58 | 31.09 30.95) | 181 |
| 14c $C_{12}H_{10}N_4S$ | 69 (iii) | >293 (decomp.) | 3080 (NH) | 222 (4.24), 228 (4.21) 241 (4.17), 255 (4.44) 259 (4.46), 268 (4.33) 286 (3.94), 315 (4.13) 340 (3.87) | 59.48 (59.53 | 4.16 4.39 | 23.12 23.01) | 243 |

[a]All compounds were recrystallised from EtOH and obtained as colorless needles. [b]Route i: HC(OEt)$_3$, TFA, r.t.; route ii: Pb(OAc)$_4$, TFA, r.t.; route iii: R$^3$C(OEt)$_3$, DMF, reflux. [c]This compound was isomerised into its [1,5-c] isomer at the temperature under mp. [d]All UV spectra were measured in EtOH. The italic values refer to wave lengths at which shoulders or inflections occur in the absorption. [e]Because this compound was isomerised into its [1,5-c] isomer in hot solvent, the elemental analysis was impossible. [f]The matrix is glycerol.

TABLE 18

Table 14 $^1$H NMR data of compounds 12b, c, 13a, b, and 14a-c

| Compd. No. | $\delta_H$ [200 MHz; (CD$_3$)$_2$SO; Me$_4$Si] |
|---|---|
| 12b | 1.79 (3 H, s, 5-Me), 2.01 (3 H, d, J = 5.5 Hz, CHMe), 6.88 (1 H, s, 6-H), 7.81 (1 H, q, J = 5.4 Hz, CHMe), 10.96 (1 H, br s, exchangeable with D$_2$O, 4-NH), 11.73 (1 H, br s, exchangeable with D$_2$O, 1-NH) |
| 12c | 1.86 (3 H, s, 5-Me), 6.97 (1 H, s, 6-H), 7.25-7.65 (3 H, m, Ph-m, pH), 7.70-7.85 (2 H, m, Ph-oH), 8.16 (1 H, s, Ph-CH), 10.60 (1 H, br s, exchangeable with D$_2$O, 4-NH), 11.85 (1 H, br s, exchangeable with D$_2$O, 1-NH) |
| 13a | 2.30 (3 H, s, 8-Me), 7.32 (1 H, s, 7-H), 9.41 (1 H, s, 3-H), 13.46 (1 H, br s, exchangeablde with D$_2$O, NH) |
| 13b | 2.21 (3 H, s, 8-Me), 3.03 (3 H, s, 3-Me), 7.10 (1 H, s, 7-H), 13.02 (1 H, br s, exchangeablde with D$_2$O, NH) |
| 14a | 2.29 (3 H, s, 8-Me), 7.59 (1 H, s, 7-H), 8.58 (1 H, s, 2-H), 13.74 (1 H, br s, exchangeablde with D$_2$O, NH) |
| 14b | 2.26 (3 H, s, 2-Me), 2.48 (3 H, s, 8-Me), 7.51 (1 H, s, 7-H), 13.49 (1 H, br s, exchangeable with D$_2$O, NH) |
| 14c | 2.35 (3 H, d, J = 1.2 Hz, 8-Me), 7.40-7.75 (4 H, m, Ph-m, pH and 7-H), 8.05-8.40 (2 H, m, Ph-oH), 13.65 (1 H, br s, exchangeable with D$_2$O, NH) |

TABLE 19

Table 15 Physical data for compounds 19a-c and 20a-c

| Compd. No.[a] (Formula) | Yield (%) (route)[b] | Mp/° C. | $\nu_{max}, \delta_{max}$ (Nujol)/cm$^{-1}$ | $\lambda_{max}$/nm (log ε/dm$^3$ mol$^{-1}$ cm$^{-1}$)[c] | Analysis (%) Calcd. (Found) C | H | N | m/z MH$^{+d}$ |
|---|---|---|---|---|---|---|---|---|
| 19a C$_6$H$_7$N$_5$ | 60 (i) | >290 (decomp.) | 3350 ($\nu_{as}$, NH$_2$) 3240 ($\nu_s$, NH$_2$) 1670 ($\delta_s$, NH$_2$) | 204 (3.54), 278 (3.55) | 48.32 (48.17 | 4.73 4.93 | 46.95 47.14) | 150 |
| 19b C$_7$H$_9$N$_5$ | 51 (i) | 210 >183 (subli.) | 3370 ($\nu_{as}$, NH$_2$) 3300 ($\nu_s$, NH$_2$) 1650 ($\delta_s$, NH$_2$) | 289 (3.60) | 51.52 (51.22 | 5.56 5.65 | 42.92 42.95) | 164 |
| 19c C$_{12}$H$_{11}$N$_5$ | 65 (i) 50 (ii) | 191 | 3290 ($\nu_{as}$, NH$_2$) 3250 ($\nu_s$, NH$_2$) 1669 ($\delta_s$, NH$_2$) | 280 (437) | 63.99 (63.77 | 4.92 5.19 | 31.09 30.89) | 226 |
| 20a C$_6$H$_7$N$_5$ | 28 (iii) 77 (iv) | 186-188 | 3330 ($\nu_{as}$, NH$_2$) 3260 ($\nu_s$, NH$_2$) 1680 ($\delta_s$, NH$_2$) | 264 (3.83), 280 (3.75) | 48.32 (48.06 | 4.73 4.93 | 46.95 47.01) | 150 |
| 20b C$_7$H$_9$N$_5$ | 34 (iii) 80 (iv) | 189 | 3340 ($\nu_{as}$, NH$_2$) 3260 ($\nu_s$, NH$_2$) 1690 ($\delta_s$, NH$_2$) | 262 (3.97), 283 (3.86) | 51.52 (51.40 | 5.56 5.62 | 42.92 42.94) | 164 |
| 20c C$_{12}$H$_{11}$N$_5$•1/4H$_2$O | 22 (iii) 72 (iv) | 212-213 | 3310 ($\nu_{as}$, NH$_2$) 3250 ($\nu_s$, NH$_2$) 1662 ($\delta_s$, NH$_2$) | 247 (430), 252(429) 276 (3.88) | 62.73 (62.55 | 5.05 5.25 | 30.48 30.25) | 226 |

[a]All compounds were recrystallised from EtOH and obtained as colorless needles. [b]Route i: R$_3$C(OEt)$_3$, ethyl cellosolve,100-120° C.; route ii: Pb(OAc)$_4$, TFA, r.t.; iii: R3C(OEt)$^3$, ethyl cellosolve, reflux; route iv: ethyl cellosolve, reflux, [c]All UV spectra were measured in EtOH. The italic values refer to wave lengths at which shoulders or inflections occur in the absorption. [d]The matrix is glycerol.

TABLE 20

Table 16 $^1$H NMR data of compounds 19a-c and 20a-c

| Compd. No. | $\delta_H$ [200 MHz; (CD$_3$)$_2$SO; Me$_4$Si] |
|---|---|
| 19a | 2.28 (3 H, s, 8-Me), 7.35 (1 H, s, 7-H), 7.71 (2 H, br s, exchangeable with D$_2$O, NH$_2$), 9.25 (1 H, s, 3-H) |
| 19b | 2.21 (3 H, s, 8-Me), 2.90 (3 H, s, 3-Me), 6.97 (2 H, br s, exchangeable with D$_2$O, NH$_2$), 7.21 (1H, s, 7-H) |
| 19c | 2.34 (3 H, s, 8-Me), 6.32 (2 H, br s, exchangeable with D$_2$O, NH$_2$), 7.40 (1 H, s, 7-H), 7.54-7.66 (3 H, m, Ph-m, pH), 7.68-7.77 (2 H, m, Ph—OH) |
| 20a | 2.29 (3 H, s, 8-Me), 7.66 (3 H, br s, exchangeable with D$_2$O, NH$_2$ and 7-H), 8.46 (1 H, s, 2-H) |
| 20b | 2.25 (3 H, s, 8-Me), 2.47 (3 H, s, 2-Me), 7.53 (2 H, br s, exchangeable with D$_2$O, NH$_2$), 7.60 (1 H, s, 7-H) |
| 20c | 2.34 (3 H, s, 8-Me), 7.50-7.60 (3 H, m, Ph-m, pH), 7.66 (2 H, br s, exchangeable with D$_2$O, NH$_2$), 7.69 (1 H, s, 7-H), 8.2-8.30 (2 H, m, Ph-oH) |

Example 7. Evaluation of the Compounds

Test Example

Regarding the synthesized triazolopyrimidine compounds, their cell proliferation inhibitory activities, as an index of antitumor acttivity, were examined. The test was performed by MTT assay (T. Mosmann, *J. Immunol. Methods,* 65, 55 (1983); M. B. Hansen, S. E. Nielsen and K. Berg, *J. Immunol. Methods,* 119, 203 (1989), which are incorporated by reference in their entirety.), and the cancer cells tested were CCRF-HSB-2 cells (human acute lymphoblastic leukemia) and KB cells (human nasal cervical cancer). Cytarabine (Ara-C, cytarabine: 4-amino-1-β-D-arabinofuranosyl-2(1H)-one) and 5-fluorouracil (5-FU, 5-fluorouracil) were used as control drugs, which are antimetabolite anticancer agents used for, for example, acute leukemia and/or gastrointestinal cancer.

In Vitro Antitumor Effect Assay
(Material)

Human acute lymphoblastic leukemia cells (T-cells) CCRF-HSB-2 and human nasopharyngeal carcinoma-derived KB cells were cultured in RPMI 1640 medium supplemented with 10% fetal bovine serum.

Test agents were dissolved in dimethyl sulfoxide to become a concentration of 10 mg/ml and stored at 4° C. These solutions were diluted with MEM-Hanks medium and used for the assay.
(Method)
1. 50 µl of the agent solution or MEM-Hanks medium was pre-filled in a 96-well plate.
2. Cells in the logarithmic growth phase were harvested, and suspension of the cells was prepared such that the cell density is $1 \times 10^5$ cells/ml (5,000 cells/50 µl/well) and the serum concentration is 20%. The suspension 50 µl was seeded to each well. The cells were cultured in a carbon dioxide incubator at 37° C. for 3 days.
3. After completion of the culture, 10 µl of MTT solution*(5 mg/ml in PBS-) was added to each well, and the cells were further cultured at 37° C. for 4 hours in a carbon dioxide incubator.

*MTT solution: 1 g of MTT (Sigma M-2128) was dissolved in 200 ml of PBS-under light shielding, and the solution was filtrated using a 0.45 µm filter, and then stored at 4° C. If insoluble components precipitated during storage, filtration was performed again.

4. After completion of the culture, 100 µl of 0.02 N HCl/50% N,N-dimethylformamide/20% SDS was added and stirred in each well to dissolve produced formazan. Its absorbance at 570 nm (test wavelength) and 690 nm (reference wavelength) was measured by a microplate reader (Tosoh MPR4Ai) and the proliferation inhibition rate was determined by the following formula.

Inhibition rate (%)=(1−*Tx*/*Cx*)×100

Tx: Absorbance of wells containing sample
Cx: Absorbance of wells containing no sample (control)
5. Inhibitory concentration showing 50% inhibition ($IC_{50}$) of samples were determined by probit analysis using a computer software.
[Evaluation]

The determined $IC_{50}$ results are shown in Table 21.

TABLE 21

Table 17 Evaluation of antitumor activity in vitro of the synthesized compounds (3a, b, 4a, b, 5a-r, 6b f, j, l, m, 9c-g, 14c and 20c)

Inhibitory concentration against tumor cell lines in vitro [ $IC_{50}$ (µM)]

| Compound No. | R | CCRF-HSB-2 | KB | Compound No. | R | CCRF-HSB-2 | KB |
| --- | --- | --- | --- | --- | --- | --- | --- |
| 3a | Et | 13 | 12 | 5a | 3,4-OCH$_2$O—C$_6$H$_3$ | 58.2 | 89.4 |
| 3b | Ph | >100 | >100 | 5p | 3-Pyridyl | 59.4 | 77.5 |
| 4a | Et | 78 | 82 | 5q | 4-Pyridy | 28.7 | 42.1 |
| 4b | Ph | >100 | >100 | 5r | 4-Naphthyl | 99.1 | >100 |
| 5a | Et | >100 | >100 | 6b | Ph | 2.71 | 7.23 |
| 5b | Ph | 48.6 | 57.1 | 6f | 4-O$_2$N—C$_6$H$_4$ | 1.45 | 1.85 |
| 5c | 4-Me—C$_6$H$_4$ | 63.1 | 42.9 | 6j | 3,4-Cl$_2$—C$_6$H$_3$ | 1.61 | 3.29 |
| 5d | 4-MeO—C$_6$H$_4$ | >100 | >100 | 6l | 4-Br—C$_6$H$_4$ | 3.47 | 5.88 |
| 5e | 2,4,6-(MeO)$_3$—C$_6$H$_2$ | >100 | >100 | 6m | 4-NC—C$_6$H$_4$ | 2.17 | 7.21 |
| 5f | 4-O$_2$N—C$_6$H$_4$ | 71.6 | 1.85 | 9c | Et | 58.2 | 48.5 |
| 5g | 2-F—C$_6$H$_4$ | 48.8 | 62.4 | 9d | Ph | 22.3 | 39.0 |
| 5h | 4-F—C$_6$H$_4$ | 55.5 | 62.4 | 9e | 3,4-Cl$_2$—C$_6$H$_3$ | 23.6 | 28.9 |
| 5i | 4-Cl—C$_6$H$_4$ | 41.8 | 50.0 | 9f | 4-Br—C$_6$H$_4$ | 31.5 | 28.5 |
| 5j | 3,4-Cl$_2$—C$_6$H$_3$ | 15.2 | 13.4 | 9g | 4-NC—C$_6$H$_4$ | 41.3 | 43.8 |
| 5k | 2-Br—C$_6$H$_4$ | 74.5 | 92.9 | 14c | Ph | 31.0 | 32.0 |
| 5l | 4-Br—C$_6$H$_4$ | 52.4 | 17.8 | 20c | Ph | 28.5 | 22.3 |
| 5m | 4-NC—C$_6$H$_4$ | >100 | 23.7 | AraC | | 0.021 | 0.12 |
| 5n | 4-HOOC—C$_6$H$_4$ | >100 | >100 | 5-FU | | 2.74 | 2.24 |

Cytarabine (AraC) used as a control drug is an anticancer agent that has extremely high toxicity and has many known side effects, and its use is limited mainly in case of that in combination with other antitumor agents. On the other hand, 5-FU is widely used as a therapeutic agent for various cancers although it has side effects. The determined $IC_{50}$s of cytarabine (AraC) on CCRF-HSB-2 cells and KB cells were 0.021 µM and 0.12 µM, respectively, and the $IC_{50}$s of 5-FU on CCRF-HSB-2 cells and KB cells were 2.74 µM and 2.24 µM, respectively. Accordingly, among the compounds having tumor cell proliferation inhibitory activity, compounds having higher cell proliferation inhibitory activity than 5-FU and having the activity as not high as cytarabine can be expected to be used as an antitumor agent having high antitumor activity and high versatility.

As shown in Table 21, with respect to CCRF-HSB-2 cells, compounds 3a, 4a, 5b-c, 5f-l, 5o-r, 6b, f, j, l, m, 9c-g, 14c and 20c had cell proliferation inhibitory activity with $IC_{50}$ equal to or less than 100 µM. In particular, compounds 6b, f, j, and m had stronger cell proliferation inhibitory activity than 5-FU.

With respect to KB cells, compounds 3a, 4a, 5b-c, 5f-m, 5o-q, 6b, f, j, l, m, 9c-g, 14c and 20c had cell proliferation inhibitory activity with $IC_{50}$ less than 100 µM. In particular, compounds 5f and 6f had stronger cell proliferation inhibitory activity than 5-FU.

Although compounds 3b, 4b, 5a, 5d, 5e, and 5n had cell proliferation inhibitory activity on both cells, their $IC_{50}$s showed greater than 100 µM.

Therefore, compounds 3a, 4a, 5b-c, 5f-m, 5o-r, 6b, f, j, l, m, 9c-g, 14c and 20c, and compositions containing the foregoing compounds have cell proliferation inhibitory activity and are useful as an antitumor agent. In particular, compounds 6b, f, j, and m and compositions containing the compounds can be expected to be used as antitumor agents having high antitumor activity and high versatility.

INDUSTRIAL APPLICABILITY

The triazolopyrimidine compounds of the present invention have antitumor activity similar to or higher than the commercially available anticancer agent 5-FU, and a composition containing the triazolopyrimidine compound of the present invention is useful as an antitumor agent for treatment of various malignant tumors.

Cross-Reference to Related Application

This is the U.S. National Stage of International Patent Application No. PCT/JP2020/014810 filed on Mar. 31, 2020, which in turn claims the benefit of priority to Japanese Patent Application No. 2019-071525, filed on Apr. 3, 2019, the disclosure of which is incorporated herein by reference in its entirety.

The invention claimed is:
1. A 5-chloro-8-methyl-[1,2,4]triazolo[1,5-c]pyrimidine compound represented by the following general formula (III):

(General formula (III))

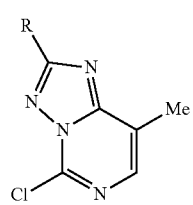

(III)

wherein R represents an aryl group.

2. A method for treating tumors, comprising administering an effective amount of a 5-chloro-8-methyl-[1,2,4]triazolo[1,5-c]pyrimidine compound represented by the following general formula (III):

(General formula (III))

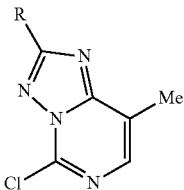

(III)

wherein R represents an aryl group.

3. A method of producing a 5-chloro-8-methyl-[1,2,4]triazolo[1,5-c]pyrimidine compound represented by the following general formula (III):

(General formula (III))

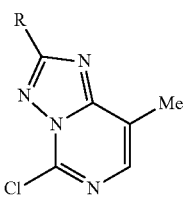

(III)

wherein R represents an aryl group,
comprising:
a step of heating an 8-methyl-[1,2,4]triazolo[1.5-c]pyrimidin-5 (6H)-one compound represented by the following general formula (II) under reflux in phosphorus oxychloride;

(General formula (II))

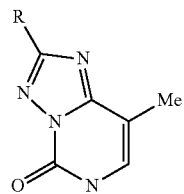

(II)

wherein R represents an aryl group.

4. The 5-chloro-8-methyl-[1,2,4]triazolo[1,5-c]pyrimidine compound according to claim 1, wherein R is a substituent represented by the following general formula (IX):

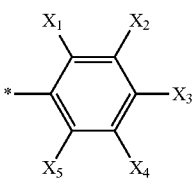

(IX)

wherein $X_1$ to $X_5$ each independently represent a group selected from the group consisting of a hydrogen atom, a halogen atom, an alkyl group, an alkoxy group, an amino group, an alkylamino group, a methylenedioxy group, a hydroxy group, a nitro group, a nitrile group, and a carboxyl group.

5. The 5-chloro-8-methyl-[1,2,4]triazolo[1,5-c]pyrimidine compound according to claim 1, wherein R is a group selected from the group consisting of phenyl group, an alkylphenyl group having an alkyl group with a carbon number of 1 to 5, an alkoxyphenyl group having an alkoxy group with a carbon number of 1 to 5, an alkylaminophenyl group having an alkylamino group with a carbon number of 1 to 5, a halogenophenyl group, a methylenedioxyphenyl group, a hydroxyphenyl group, a nitrophenyl group, a cyanophenyl group or a carboxyphenyl group.

6. The 5-chloro-8-methyl-[1,2,4]triazolo[1,5-c]pyrimidine compound according to claim 1, wherein R is a halogenophenyl group, a nitrophenyl group, a hydroxyphenyl group or a cyanophenyl group.

7. The 5-chloro-8-methyl-[1,2,4]triazolo[1,5-c]pyrimidine compound according to claim 1, wherein R is a bromophenyl group, a chlorophenyl group or a fluorophenyl group.

8. The 5-chloro-8-methyl-[1,2,4]triazolo[1,5-c]pyrimidine compound according to claim 1, wherein R is a phenyl group, a 4-nitrophenyl group, a 3,4-dichlorophenyl group, 4-bromophenyl group or a 4-cyanophenyl group.

9. The method according to claim 2, wherein R is a halogenophenyl group, a nitrophenyl group, a hydroxyphenyl group or a cyanophenyl group.

10. The method according to claim 2, wherein R is a phenyl group, a 4-nitrophenyl group, a 3,4-dichlorophenyl group, 4-bromophenyl group or a 4-cyanophenyl group.

* * * * *